United States Patent
Mitchell et al.

(10) Patent No.: US 8,771,290 B2
(45) Date of Patent: Jul. 8, 2014

(54) MICROSTEREOTACTIC TABLE

(75) Inventors: Jason E. Mitchell, Greenbrier, TN (US); Robert F. Labadie, Bozeman, TN (US); J. Michael Fitzpatrick, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1073 days.

(21) Appl. No.: 12/713,648

(22) Filed: Feb. 26, 2010

(65) Prior Publication Data

US 2010/0179564 A1 Jul. 15, 2010

Related U.S. Application Data

(63) Continuation-in-part of application No. 11/782,305, filed on Jul. 24, 2007, now Pat. No. 7,981,122.

(60) Provisional application No. 60/832,776, filed on Jul. 24, 2006.

(51) Int. Cl.
A61B 19/00 (2006.01)

(52) U.S. Cl.
USPC ........................................ 606/130; 248/181.1

(58) Field of Classification Search
USPC ......... 606/130; 248/188–188.4, 177.1, 181.1; 600/415, 417
See application file for complete search history.

(56) References Cited

U.S. PATENT DOCUMENTS

| | | | |
|---|---|---|---|
| 3,881,675 A | 5/1975 | Matchett | |
| 4,608,977 A | 9/1986 | Brown | |
| 4,613,324 A | 9/1986 | Ghajar | |
| 4,821,716 A | 4/1989 | Ghajar | |
| 5,776,143 A * | 7/1998 | Adams | 606/130 |
| 5,776,144 A * | 7/1998 | Leysieffer et al. | 606/130 |
| 6,298,262 B1 | 10/2001 | Franck et al. | |
| 6,327,491 B1 | 12/2001 | Franklin et al. | |
| 6,459,927 B1 | 10/2002 | Franklin et al. | |
| 6,579,281 B2 | 6/2003 | Palmer | |
| 6,738,657 B1 | 5/2004 | Franklin et al. | |
| 6,893,447 B2 | 5/2005 | Dominguez | |
| 2002/0084389 A1* | 7/2002 | Larson | 248/188.1 |
| 2004/0167530 A1* | 8/2004 | Hamel | 606/86 |
| 2005/0119639 A1 | 6/2005 | McCombs et al. | |

(Continued)

OTHER PUBLICATIONS

Maurer CR Jr et al., (1997) Registration of head volume images using implantable fiducial markers. IEEE Trans Med Imaging 16:447-462. doi:10.1109/42.611354.

(Continued)

*Primary Examiner* — Katherine Dowe
(74) *Attorney, Agent, or Firm* — Tim Tingkang Xia, Esq.; Morris Manning & Martin, LLP

(57) ABSTRACT

The present invention, in another aspect, relates to a microstereotactic table. In one embodiment, the microstereotactic table includes a plate member having a first surface, an opposite, second surface, a body portion defined therebetween, a plurality of leg members, each of them removably engaged with the plate member, respectively, and a passage is formed between the first surface and the opposite, second surface of the body portion of the plate member and along a longitudinal axis, wherein a step is formed within the passage, and wherein the step is formed such that the distance from the step to one of the first surface and the opposite, second surface along the longitudinal axis is a predetermined length.

11 Claims, 15 Drawing Sheets

(56) References Cited

U.S. PATENT DOCUMENTS

| | | |
|---|---|---|
| 2006/0086868 A1 | 4/2006 | White |
| 2007/0106305 A1 | 5/2007 | Kao et al. |
| 2007/0191852 A1 | 8/2007 | Shimko et al. |

OTHER PUBLICATIONS

Woerdeman PA et al., (2007) Application accuracy in frameless image-guided neurosurgery: a comparison study of three patient-to-image registration methods. J Neurosurg 106(6):1012-1016. Doi:10.3171/jns.2007.106.6.1012.

Maciunas RJ et al., (1994) The application accuracy of stereotactic frames. Neurosurgery 35:682-694. doi:10.1097/00006123-199410000-00015.

Yu C et al., (2001) A phantom study of the geometric accuracy of computed tomographic and magnetic resonance imaging stereotactic localization with the Leksell stereotactic system. Neurosurgery 48:1092-1099. doi:10.1097/00006123-200105000-00025.

Bjartmarz H et al., (2007) Comparison of accuracy and precision between frame-based and frameless stereotactic navigation for deep brain stimulation electrode implantation. Stereotact Funct Neurosurg 85:235-242. doi:10.1159/000103262.

Balachandran R et al., (2009) Accuracy evaluation of MicroTargeting™ platforms for deep-brain stimulation using virtual targets. IEEE Trans Biomed Eng 56(1):37-44.

Henderson JM et al., (2004) The application accuracy of a skull-mounted trajectory guide system for image-guided functional neurosurgery. Comput Aided Surg 9:155-160. doi:10.1080/10929080500050249.

Balachandran R et al., (2007) Evaluation of targeting frames for deep-brain stimulation using virtual targets. In: IEEE international symposium on biomedical imaging: from Nano to Macro, 2007, pp. 1184-1187.

Labadie RF et al., (2008) Clinical validation of percutaneous cochlear implant surgery: Initial report. Laryngoscope 118(6):1031-1039.

Liu X et al., (2003) Marker orientation in fiducial registration. In: Proceedings SPIE Medical Imaging 2003, San Diego, CA, vol. 5032. pp. 1176-1185.

Labadie RF et al., (2005) Minimally-invasive, image-guided, facial-recess approach to the middle ear: Demonstration of the concept of percutaneous cochlear access in vitro. Otol Neurotol 26:557-562. doi:10.1097/01.mao.0000178117.61537.5b.

Warren FM et al., (2007) Percutaneous cochlear access using bone-mounted, customized drill guides: demonstration of concept in vitro. Otol Neurotol 28(3):325-329. Doi:10.1097/01.mao.0000253287.86737.2e.

Noble JH et al., (2007) Determination of drill paths for percutaneous cochlear access accounting for target positioning error. In: Proceedings of Medical Imaging 2007, San Diego.

Labadie RF et al., (2009) Clinical validation study of percutaneous cochlear access using patient-customized, microstereotactic frames. Otology & Neurotology, Accepted for presentation at the 2009 AOS/COSM Spring Meeting Scientific Sessions, Phoenix, AZ, May 2009.

\* cited by examiner

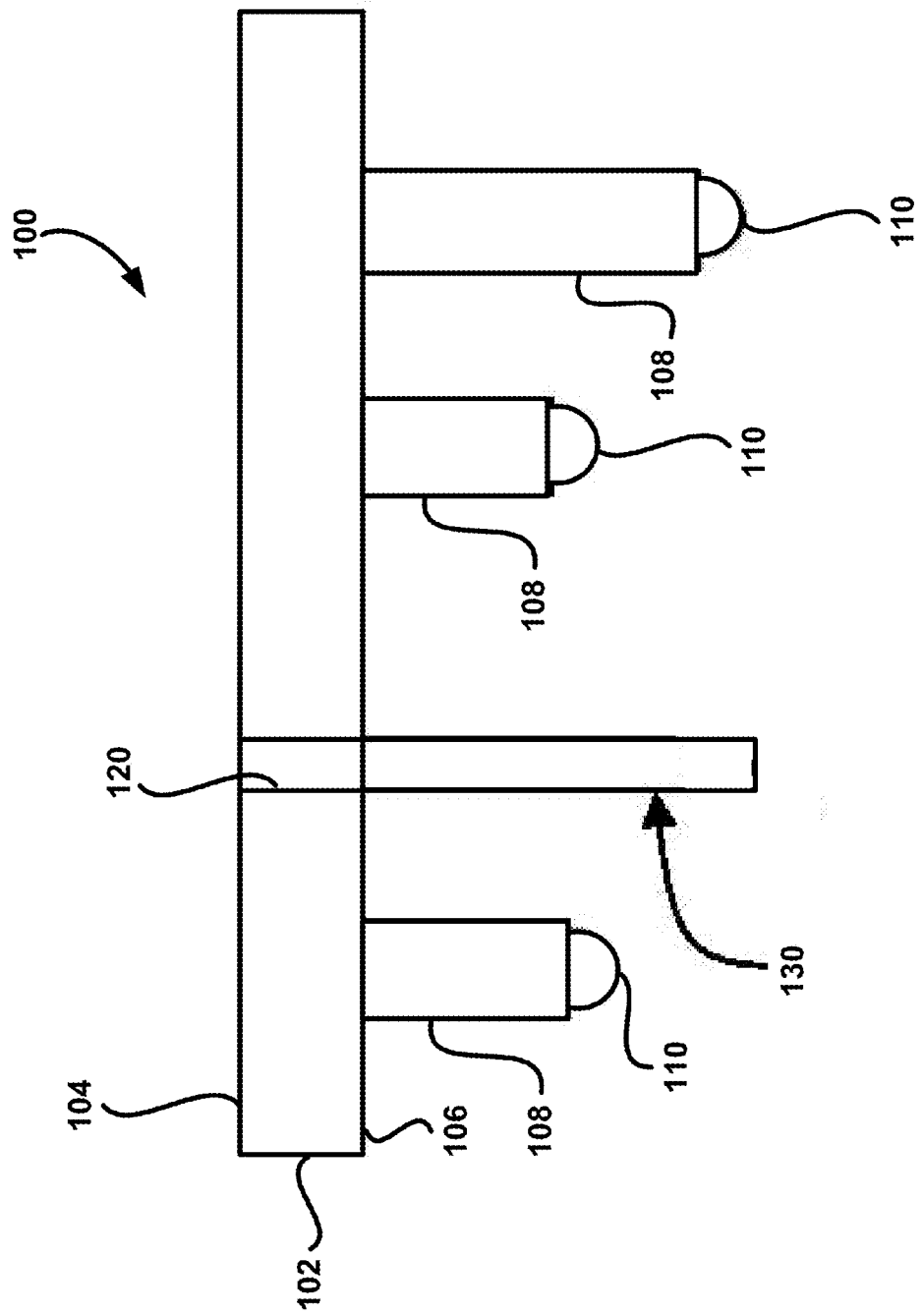

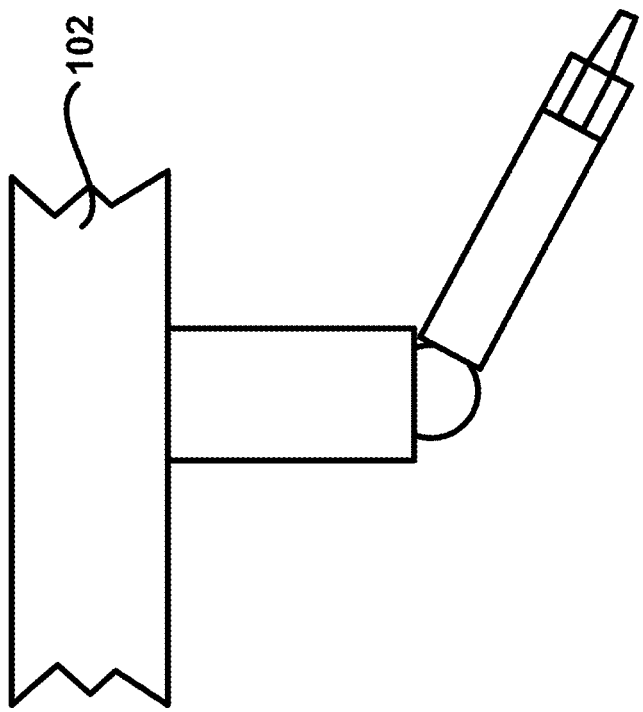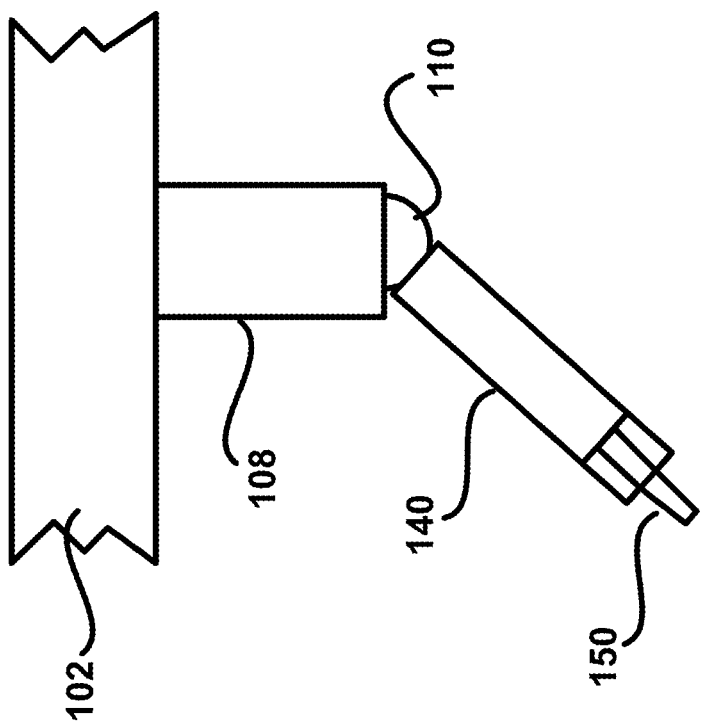
FIG. 1b

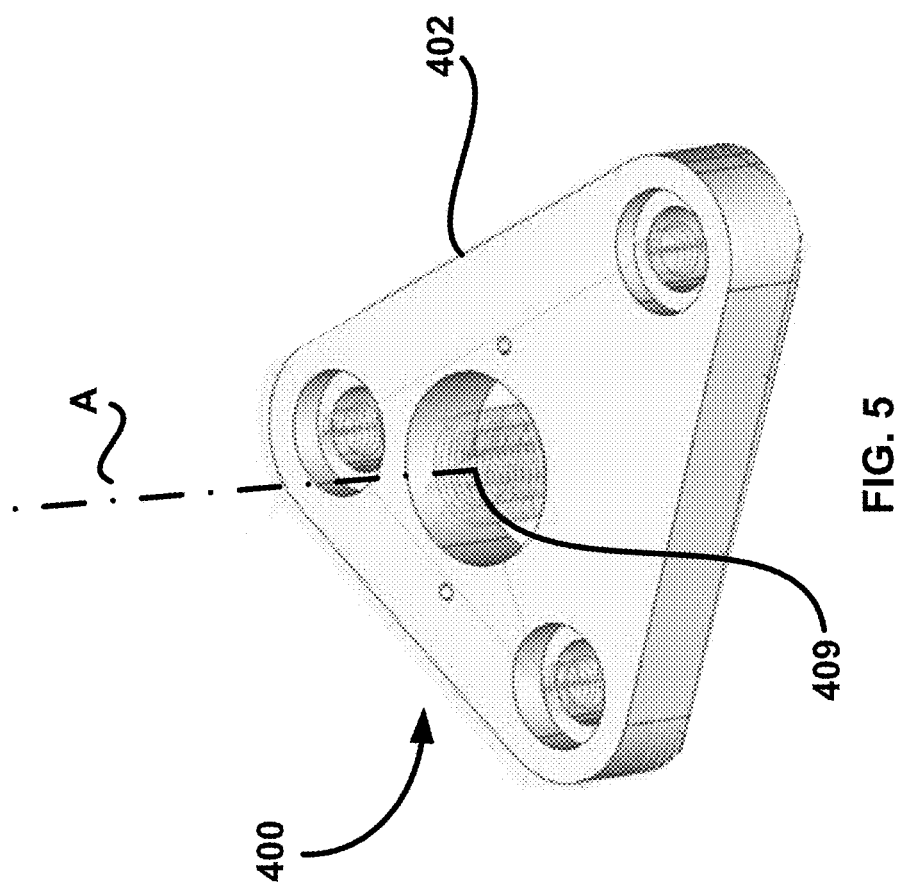

MICROSTEREOTACTIC TABLE

CROSS-REFERENCE TO RELATED PATENT APPLICATION

This application is a continuation-in-part of U.S. patent application Ser. No. 11/782,305, filed on Jul. 24, 2007, entitled "Adjustable Surgical Platform and Surgical Instrument Using Same" by J. Michael Fitzpatrick, Robert F. Labadie and Jason E. Mitchell, which itself claims the benefit, pursuant to 35 U.S.C. §119(e), of U.S. provisional patent application Ser. No. 60/832,776, filed Jul. 24, 2006, entitled "Adjustable Surgical Platform, Surgical Instrument, System and Methods of Making and Using Same," by Robert F. Labadie, and J. Michael Fitzpatrick, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT OF FEDERALLY-SPONSORED RESEARCH

This invention was made with government support under contract EB002886 awarded by National Institutes of Health. The government has certain rights in the invention.

FIELD OF THE INVENTION

The present invention generally relates to a microstereotactic table. More particularly, the present invention relates to a microstereotactic table usable with a surgical instrument for providing an access to a target of interest of a living subject, and a process of how to manufacture it.

BACKGROUND OF THE INVENTION

The therapies of deep-brain stimulation (DBS) and auditory neuron stimulation have gained significantly clinical popularity over the past decades. The former has significant applications in the treatment of a variety of brain-controlled disorders, including movement disorders, while the latter has applications in the treatment of hearing impairment.

Generally, such treatments involve identifying a corresponding physiological target to be stimulated, surgically drilling a burr hole in the patient's skull or temporal bone to create an access to the corresponding physiological target, placing an electronic device in the corresponding physiological target through the drilled burr hole, and then applying appropriate stimulation signals through the implanted electrode device to the physiological target.

The placement portion of the treatment, involving stereotactic neurosurgical methodology, is very critical, and has been the subject of much attention and research. In particular, finding the deep brain target and then permanently placing the electrode lead so that it efficiently stimulates such target is very important.

Stereotactic neurosurgery is a field of neurosurgery in which a probe is advanced through a burr hole to a target of interest by means of a mechanical device attached to the skull with aiming based on pre-operative images. The probe may be a biopsy needle or an implantable device, but it is geometrically rigid, so that its tip, or working end portion, can be brought to a target of interest specified on a pre-operative image, by means of a geometrical calculation. For the past decade, the field has been advancing from the imposition of large, classical metal frames, which encompass the entire head of a patient, to the attachment of small platforms placed only over an entry site to reduce patient discomfort, facilitate surgical access, allow multiple targeting during one surgery via multiple platforms, and reduce procedure time, while maintaining the same level of accuracy.

More specifically, image-guided surgical (IGS) technology allows surgeons to navigate based upon registration of pre-intervention images (e.g., CT or MRI scans) to intraoperative anatomy. In the last 15 years, IGS systems using real-time tracking of surgical instruments have been FDA-approved and CE-marked for endoscopic sinus surgery and neurosurgical intervention. While versatile in allowing free-hand navigation during surgery, the accuracy of such IGS systems depends upon the type and placement of fiducial markers used to register to the pre-intervention scans. Accuracy of systems range from 1 to 2 mm for those which utilize bone-implanted fiducial markers [1] to 2-5 mm for those which depend upon skin-affixed fiducial marker systems (e.g., adhesively affixed skin markers and laser scanning of skin surfaces) [2].

For clinical applications where only a single or finite number of targets are to be accessed, the use of a highly versatile, real-time tracking IGS system may not offer the best solution. For such applications—biopsy and/or placement of electrodes into precise intracranial locations—the traditional stereotactic frame provides better overall accuracy without the need for elaborate tracking systems. The stereotactic frame is rigidly attached to a patient during both imaging and surgical intervention using sharp pins that pierce the skull. It offers increased levels of accuracy because the frame provides both the fiducial system and the targeting system. To date the most successful fiducial component of the stereotactic frame is the N-frame of Brown's design [3]. Target locations are determined by triangulation relative to the N-frame. Accuracy for such traditional stereotactic frames approaches 1 mm or better [4-6]. However, a major drawback is the bulky nature of the frames which are extraordinarily uncomfortable for patients and often obstructive of surgical exposure in the operating room.

To overcome the drawbacks of traditional stereotactic frames, microstereotactic frames were introduced. One such frame is a patient-customized microstereotactic frame [7] that mounts on bone-implanted anchors, which serve also as fiducial markers for targeting purposes. Now commercially available, the "StarFix microTargeting Platform" (FHC Inc., Bowdoin, Me., USA), henceforth referred to as the Starfix, is FDA-approved for placement of deep brain stimulating (DBS) electrodes [8]. In practice, a patient has at least three bone-implanted anchors placed, following which a CT, and possibly an MRI, is obtained. These fiducial markers are small and subcutaneously placed, so the patient can leave the medical facility between imaging and surgical intervention and return to normal activities of daily living. In the patient's absence, the surgical target is identified, as a path from the surface of the skull to the target. Next, a microstereotactic frame that mounts on the anchors and achieves the desired trajectory is manufactured via rapid prototyping. Because rapid-prototyping technology requires expensive equipment and expertise to perform, the current paradigm employs a centralized manufacturing facility from which the customized frames are shipped. Shipping imparts a delay of at least 48 h from the time of anchor placement until the time of surgical intervention. This delay is a disadvantage relative to the traditional stereotactic frame, but holds out the benefit of decreased human error as no adjustments are necessary once the Starfix is mounted. A recent phantom study indicated that the Starfix as used for DBS surgeries, provides submillimetric accuracy [9].

Another microstereotactic frame FDA-approved for DBS surgeries is the "NexFrame" (Medtronic, Minneapolis, Minn., USA) [10]. Unlike the Starfix, which is custom built for each patient, the NexFrame is universally adaptable to patient anatomy through the use of a real-time tracking IGS system, which is necessary to localize fiducials and aim the device. While the NexFrame system can be used immediately after placement of markers and CT/MRI scanning, it requires the availability of an IGS system, which costs upwards of $100,000. Resultant accuracy is limited by the tracking error inherent to the IGS system and human error during alignment of the device. A recent phantom study indicated that the NexFrame provides accuracy on the order of just over one millimeter [11].

Therefore, a heretofore unaddressed need still exists in the art to address the aforementioned deficiencies and inadequacies.

SUMMARY OF THE INVENTION

The present invention, in one aspect, relates to a microstereotactic table usable with a surgical instrument for providing an access to a target of interest of a living subject. In one embodiment, the surgical instrument is a surgical drill, and the microstereotactic table includes a planar plate member having a first surface, an opposite, second surface, a body portion defined therebetween;

a first leg member removably engaged with the planar plate member;

a second leg member removably engaged with the planar plate member; and a third leg member removably engaged with the planar plate member, wherein the first, second and third leg members are positioned such that each of them is located at an apex of a triangle $\Delta$, respectively, wherein the first leg member and the second leg member define a first line $S_1$, the second leg member and the third leg member define a second line $S_2$, and the third leg member and the first leg member define a third line $S_3$, and wherein the triangle $\Delta$ is defined by the first line $S_1$, the second line $S_2$, and the third line $S_3$, wherein the planar plate member defines a passage between the first surface and the opposite, second surface of the body portion and along a longitudinal axis A, wherein cross-sectionally the center of the passage is located inside the triangle $\Delta$, and wherein the passage is configured, in operation, to be coincided along a planned trajectory and allow a surgical instrument to pass through the passage to reach the target of interest of the living subject.

In one embodiment, each of the first, second and third leg members has a base member having a first end, and an opposite, second end, and a body portion defined therebetween; and an extended member having a first end, and an opposite, second end, and a body portion defined therebetween, wherein the base member and the extended member are configured such that the extended member is three-dimensionally rotatably engaged at its first end with the base member at the second end of the base member.

In one embodiment, the base member has a cap portion formed proximate to the first end of the base member;

a bottom portion formed proximate to the second end of the base member, wherein a partially spherical recess is formed in the bottom portion;

the body portion has an opening formed thereon and extending longitudinally from the second end of the base member towards to the first end of the base member; and a Gripper having a first end hook portion, an opposite second hook portion and a base portion, wherein the first end hook portion and the second hook portion project away from the base portion in parallel and define an opening therebetween with a distance $d_g$, and wherein the Gripper is configured to allow it be received in the opening of the body portion with the base portion being supported by the bottom portion.

Moreover, the base member has a bore formed along its longitudinal axis, and a thumbscrew that is received in the bore for tightening the Gripper.

Additionally, in one embodiment, the extended member further has:

an at least partially spherical top portion formed at the first end of the extended member, wherein the at least partially spherical top portion has a diameter $d_s$; and an engagement portion formed at the second end of the extended member for engaging a bone anchor, wherein the at least partially spherical top portion is formed such that $d_g < d_s$. The at least partially spherical top portion of the extended member is configured to be received in the partially spherical recess of the bottom portion of the base member, such that the extended member is three-dimensionally rotatable relative to the base member and is also engaged at the second end of the base member by the first end hook portion and the second hook portion of the Gripper.

The engagement portion formed at the second end of the extended member is formed with a configuration that is complimentary to the configuration of a top portion of a corresponding bone anchor for a mechanical engagement.

In one embodiment, the base members of the first, second and third leg members are parallel to each other. Moreover, the base members of the first, second and third leg members are perpendicular to at least one of the first surface and the second surface of the planar plate member.

The present invention, in another aspect, relates to a microstereotactic table. In one embodiment, the microstereotactic table includes a plate member having a first surface, an opposite, second surface, a body portion defined therebetween;

a first leg member, a second leg member, and a third leg member, each of them removably engaged with the plate member and located at an apex of a triangle $\Delta$, respectively, wherein the first leg member and the second leg member define a first line $S_1$, the second leg member and the third leg member define a second line $S_2$, and the third leg member and the first leg member define a third line $S_3$, and wherein the triangle $\Delta$ is defined by the first line $S_1$, the second line $S_2$, and the third line $S_3$, wherein the plate member defines a passage between the first surface and the opposite, second surface of the body portion and along a longitudinal axis A, wherein cross-sectionally the center of the passage is located inside the triangle $\Delta$.

In one embodiment, each of the first, second and third leg members has a base member; and an extended member, wherein the base member and the extended member are configured such that the extended member is three-dimensionally rotatably engaged with the base member.

In one embodiment, the base member has a cap portion formed proximate to a first end of the base member;

a bottom portion formed proximate to an opposite, second end of the base member, wherein a partially spherical recess is formed in the bottom portion;

a body portion that has an opening formed thereon and extending longitudinally from the second end of the base member towards to the first end of the base member; and a resilient member configured to be received in the opening of the body portion and defining an opening with a distance $d_g$.

Moreover, in one embodiment, the base member has a bore formed along its longitudinal axis, and a tightening member that is removably received in the bore for positioning the resilient member.

Furthermore, the extended member further has an at least partially spherical top portion formed at the first end of the extended member, wherein the at least partially spherical top portion has a diameter $d_s$; and an engagement portion formed at the second end of the extended member for engaging a bone anchor, wherein the at least partially spherical top portion is formed such that $d_g < d_s$. The at least partially spherical top portion of the extended member is configured to be received in the partially spherical recess of the bottom portion of the base member, such that the extended member is three-dimensionally rotatable relative to the base member and is also engaged at the second end of the base member by the resilient member.

In one embodiment, the resilient member is a Gripper having a first end hook portion, an opposite second hook portion and a base portion, wherein the first end hook portion and the second hook portion project away from the base portion in parallel and define the opening therebetween with a distance $d_g$.

In one embodiment, the tightening member is a thumbscrew.

In one embodiment, the engagement portion formed at the second end of the extended member is formed with a configuration that is complimentary to the configuration of a top portion of a corresponding bone anchor for a mechanical engagement.

In one embodiment, the base members of the first, second and third leg members are parallel to each other. The plate member is planar and has a first surface and an opposite, second surface, and wherein the base members of the first, second and third leg members are perpendicular to at least one of the first surface and the second surface of the plate member.

The present invention, in a further aspect, relates to a leg member for supporting a microstereotactic table. In one embodiment, the leg member includes a base member; and an extended member, wherein the base member and the extended member are configured such that the extended member is three-dimensionally rotatably engaged with the base member.

In one embodiment, the base member has a cap portion formed proximate to a first end of the base member;

a bottom portion formed proximate to an opposite, second end of the base member, wherein a partially spherical recess is formed in the bottom portion;

a body portion that has an opening formed thereon and extending longitudinally from the second end of the base member towards to the first end of the base member; and a resilient member configured to be received in the opening of the body portion and defining an opening with a distance $d_g$. Furthermore, the base member has a bore formed along its longitudinal axis, and a tightening member that is removably received in the bore for positioning the resilient member.

In one embodiment, the extended member further has an at least partially spherical top portion formed at the first end of the extended member, wherein the at least partially spherical top portion has a diameter $d_s$; and an engagement portion formed at the second end of the extended member for engaging a bone anchor, wherein the at least partially spherical top portion is formed such that $d_g < d_s$. The at least partially spherical top portion of the extended member is configured to be received in the partially spherical recess of the bottom portion of the base member, such that the extended member is three-dimensionally rotatable relative to the base member and is also engaged at the second end of the base member by the resilient member. In one embodiment, the resilient member is a Gripper having a first end hook portion, an opposite second hook portion and a base portion, wherein the first end hook portion and the second hook portion project away from the base portion in parallel and define the opening therebetween with a distance $d_g$.

In one embodiment, the tightening member is a thumbscrew.

In one embodiment, the engagement portion formed at the second end of the extended member is formed with a configuration that is complimentary to the configuration of a top portion of a corresponding bone anchor for a mechanical engagement.

The present invention, in yet another aspect, relates to a process for a making microstereotactic table usable with a surgical instrument for providing an access to a target of interest of a living subject. In one embodiment, the process includes the steps of:

providing three bone anchors, each of the bone anchors having a top portion and a tip portion;

providing three leg members, each of the leg members comprising:

a base member; and an extended member having an at least partially spherical top portion configured for rotatably and removably engagable with the base member and an engagement portion for engaging a bone anchor;

implanting the three bone anchors into bones surrounding a target of interest T such that a first bone anchor and a second bone anchor define a first line $T_1$, the second bone anchor and a third bone anchor define a second line $T_2$, and the third bone anchor and the bone anchor define a third line $T_3$, wherein an area $\Delta$ is defined by the first line $T_1$, the second line $T_2$, and the third line $T_3$ enclose an area O, and wherein the target of interest T is located inside the area O;

engaging each of the three extended members with a corresponding bone anchor such that each pair of an extended member and a corresponding bone anchor form a marker, where the center of the at least partially spherical top portion of the extended member of a marker represents the location of the marker;

acquiring a CT scan image spanning the target of interest and all of the markers;

obtaining the locations of the markers from the acquired CT scan image;

obtaining the location of the target of interest from the acquired CT scan image to establish a trajectory that is ending at the location of the target of interest; and constructing a microstereotactic table by using the obtained information of the locations of the markers, the location of the target of interest and the established trajectory, wherein the constructed microstereotactic table comprises a plate member that defines three holes, each of the three holes located at a position corresponding to a location of one of the markers, wherein the plate member further defines a passage along a longitudinal axis A of the plate member, wherein the passage is positioned in a path that is coincident with the trajectory.

In one embodiment, the step of obtaining the locations of the markers from the acquired CT scan image includes the step of localizing the center of the at least partially spherical top portion of each extended member.

The present invention, in another aspect, relates to a microstereotactic table. In one embodiment, the microstereotactic table includes:

a plate member having a first surface, an opposite, second surface, a body portion defined therebetween;

a plurality of leg members, each of them removably engaged with the plate member, respectively, a passage is formed between the first surface and the opposite, second surface of the body portion of the plate member and along a longitudinal axis A, wherein a step is formed within the passage, and wherein the step is formed such that the distance from the step to one of the first surface and the opposite, second surface along the longitudinal axis A is a predetermined length.

In one embodiment, each of the plurality of leg members has a base member, and an extended member, wherein the base member and the extended member are configured such that the extended member is three-dimensionally rotatably engaged with the base member.

The base member has a cap portion formed proximate to a first end of the base member, and a bottom portion formed proximate to an opposite, second end of the base member, wherein a partially spherical recess is formed in the bottom portion. The base member further has a body portion that has an opening formed thereon and extending longitudinally from the second end of the base member towards to the first end of the base member, and a resilient member configured to be received in the opening of the body portion and defining an opening. The base member, moreover, has a bore formed along its longitudinal axis.

The extended member further has an at least partially spherical top portion formed at the first end of the extended member, and an engagement portion formed at the second end of the extended member for engaging a bone anchor. The at least partially spherical top portion of the extended member is configured to be received in the partially spherical recess of the bottom portion of the base member, such that the extended member is three-dimensionally rotatable relative to the base member and is also engaged at the second end of the base member by the resilient member.

The resilient member, in one embodiment, comprises a gripper having a first end hook portion, an opposite second hook portion and a base portion, wherein the first end hook portion and the second hook portion project away from the base portion in parallel and define an opening therebetween.

A tightening member is removably received in the bore for positioning the resilient member. In one embodiment, the tightening member is a thumbscrew.

In one embodiment, the engagement portion formed at the second end of the extended member is formed with a configuration that is complimentary to the configuration of a top portion of a corresponding bone anchor for a mechanical engagement.

In one embodiment, the base members of the plurality of leg members are parallel to each other, and are perpendicular to at least one of the first surface and the second surface of the plate member, and the step formed within the passage.

The present invention, in yet another aspect, relates to a process for a making microstereotactic table usable with a surgical instrument for providing an access to a target of interest of a living subject. In one embodiment, the process includes the steps of:

providing a plurality of bone anchors, each of the bone anchors having a top portion and a tip portion;

providing a plurality of leg members, each of the leg members comprising:

a base member; and an extended member having an at least partially spherical top portion configured for rotatably and removably engagable with the base member and an engagement portion for engaging a bone anchor;

implanting the plurality of bone anchors into bones surrounding a target of interest T;

engaging each of the extended members of the plurality of leg members with a corresponding bone anchor, respectively, such that each pair of an extended member and a corresponding bone anchor form a marker, where the center of the at least partially spherical top portion of the extended member of a marker represents the location of the marker;

acquiring a CT scan image spanning the target of interest and all of the markers;

obtaining the locations of the markers from the acquired CT scan image;

obtaining the location of the target of interest from the acquired CT scan image to establish a trajectory that is ending at the location of the target of interest; and constructing a microstereotactic table by using the obtained information of the locations of the markers, the location of the target of interest and the established trajectory, wherein the constructed microstereotactic table comprises a plate member that defines a plurality of holes, each of the plurality of holes located at a position corresponding to a location of one of the markers, wherein the plate member further defines a passage along a longitudinal axis A of the plate member, wherein the passage is positioned in a path that is coincident with the trajectory, and wherein a step is formed within the passage.

In one embodiment, the step of obtaining the locations of the markers from the acquired CT scan image comprises the step of localizing the center of the at least partially spherical top portion of each extended member.

In one embodiment, the step formed within the passage is formed such that the distance from the step to the location of the target of interest along the longitudinal axis A is a predetermined length.

In one embodiment, the microstereotactic table is constructed with a first surface, and an opposite, second surface such that at least one of them is parallel to the step along the longitudinal axis A.

In one embodiment, the process further includes the step of calculating the positions of the plurality of holes based on the obtained locations of the markers from the acquired CT scan image.

In one embodiment, the process further includes the step of calculating the position of the passage based on the obtained location of the passage from the acquired CT scan image.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein:

FIG. 1 shows (a) a microstereotactic table according to one embodiment of the present invention, where three spherical fiducial markers are used. The tabletop is elevated above the spherical fiducial markers using legs to orient it perpendicularly to the trajectory; (b) two example configurations of bone-implanted anchor and extender for the spherical fiducial marker illustrating that specific location and orientation of the anchors are relatively unimportant according to one embodiment of the present invention.

FIG. 5 shows a microstereotactic table with CNC tool paths shown therein according to one embodiment of the present invention.

DETAILED DESCRIPTION OF THE INVENTION

Figure 2:
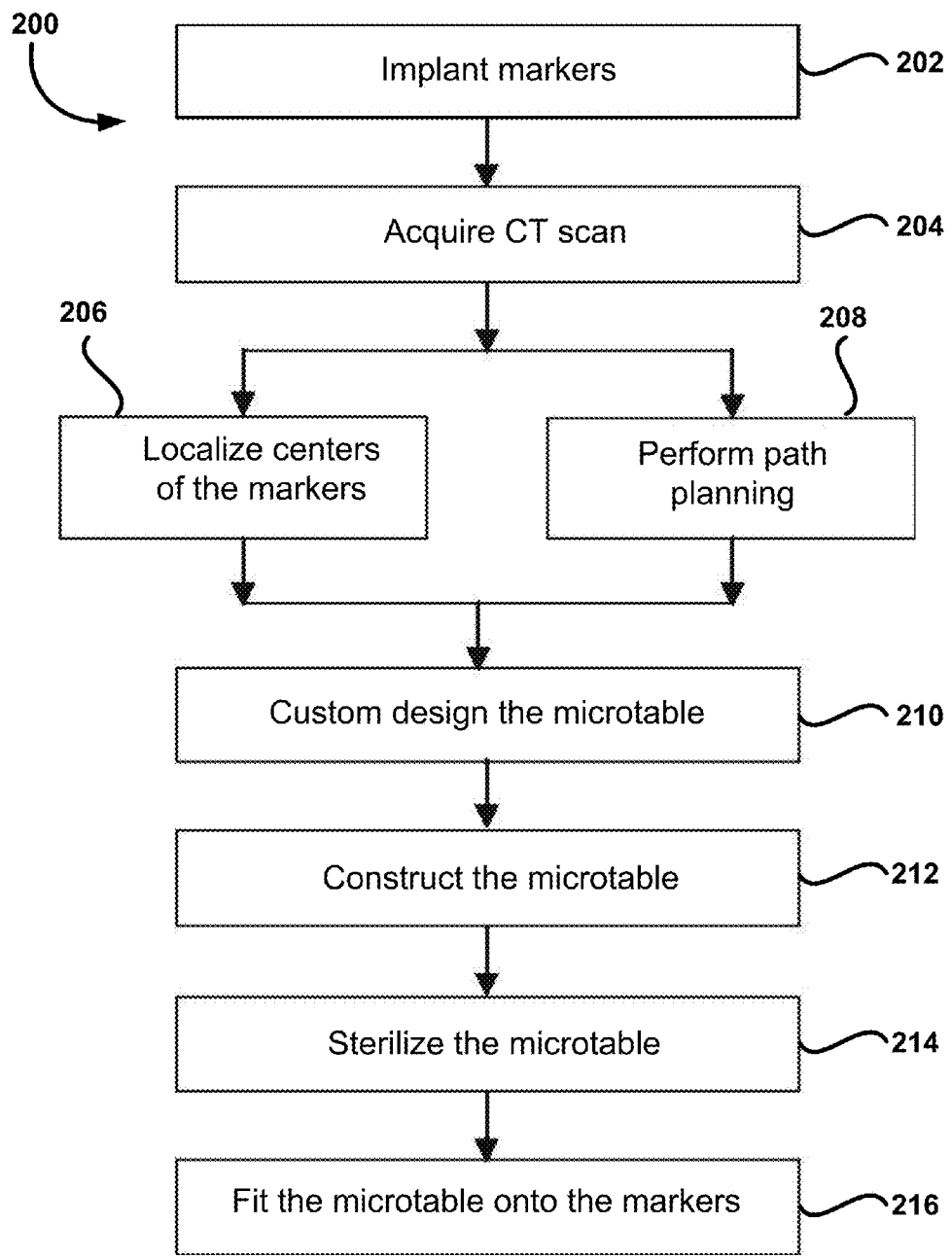
FIG. 2 shows a flowchart illustrating one or more steps involved to practice one embodiment of the present invention for a clinical application.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

Additionally, some terms used in this specification are more specifically defined below, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention. Additionally, certain theories are proposed and disclosed herein; however, in no way they, whether they are right or wrong, should limit the scope of the invention.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

The description will be made as to the embodiments of the present invention in conjunction with the accompanying drawings of FIGS. 1-10. In accordance with the purposes of this invention, as embodied and broadly described herein, this invention, in one aspect, relates to a surgical instrument for providing an access to a target of interest of a living subject. The living subject can be a human or an animal. The target of interest can be areas in a deep brain, a middle ear or other anatomical structures of the living subject. The target of interest can also be areas in other body parts of a living subject.

In this disclosure a new microstereotactic frame is introduced, which combines the advantages of both the Starfix and the NexFrame systems, while overcoming each system's disadvantages. This stereotactic device is termed as a "Microtable" in the disclosure from time to time. Like the Starfix, the microtable is customized in a rigid form for each patient, minimizing human error in clinical application. Like the NexFrame, the microtable is customized on site thus eliminating the turnover time of the Starfix. But the microtable, as further described below and defined by claims, has distinctive and novel features over the Starfix, NexFrame, other existing technologies and any combination of them. Among other things, a microstereotactic table 100 usable with a surgical instrument for providing an access to a target of interest of a living subject is disclosed herein as well as relevant data related to phantom testing mimicking one proposed clinical use—surgical targeting of the cochlea to place a cochlear implant electrode. The phantom testing shows submillimetric accuracy for this application.

Referring now to FIGS. 1-10, and first to FIG. 1, a microstereotactic table 100 usable with a surgical instrument for providing an access to a target of interest of a living subject is shown according to various embodiments of the present invention. In one embodiment, the surgical instrument can be a surgical drill (not shown in FIG. 1), and the microstereotactic table 100 has a plate member 102 having a first surface 104, an opposite, second surface 106, a body portion defined therebetween. The plate member 102 shown here is a planar plate member 102; however, the plate member 102 can have other geometric shape; for example, it may have one or more grooves, steps, projections, or any combinations of them in one or more surfaces of the plate member 102.

Additionally, the microstereotactic table 100 has one or more leg members 108 protruding from the second surface 106 of the plate member 102 away from the body portion of the plate member 102. For each leg member 108, there is a corresponding at least partially spherical top portion 110 formed at a distal end of that leg member 108 away from the body portion of the plate member 102. Moreover, an opening 120 is defined in the body portion of the plate member 102 to receive a passage member 130 therein and passing through. As further discussed below, the positions of the leg members 108 relative to each other in three dimensions and relative to the plate member 102 are case-specific.

Figure 4A:
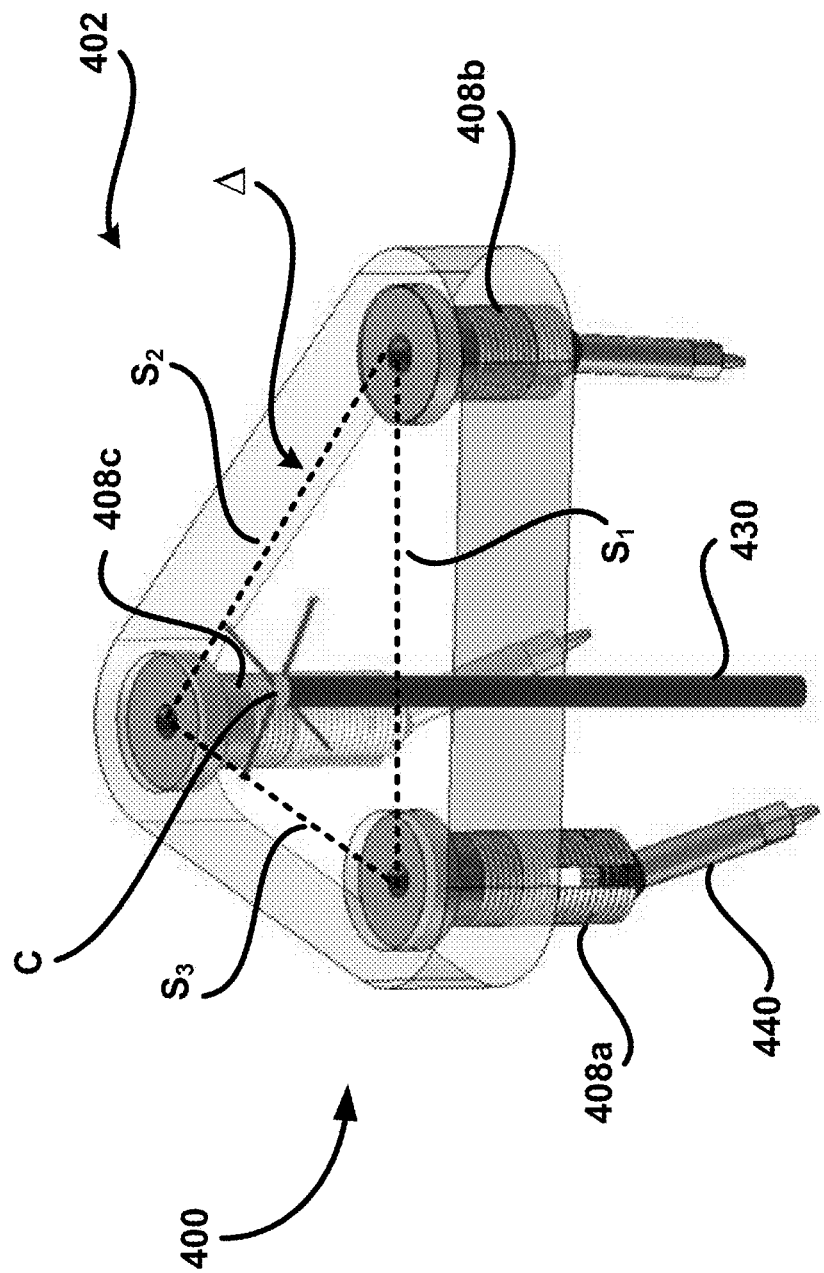
FIG. 4 shows (a) countersinking of the legs or leg members such that the tabletop is perpendicular to the trajectory according to one embodiment of the present invention; and (b) a sectional view of a microstereotactic table with leg members according to one embodiment of the present invention in relation to the target of interest.

Referring now to FIG. 4, according to one embodiment of the present invention, a microstereotactic table 400 has three leg members 408a, 408b, 408c. In this embodiment, the first leg member 408a is removably engaged with a plate member 402 and received at least partially in a first hole formed in the plate member 402, the second leg member 408b is removably engaged with the plate member 402 and received at least partially in a second hole formed in the plate member 402, and the third leg member 408c is also removably engaged with the plate member 402 and received at least partially in a third hole formed in the plate member 402. The first, second and third leg members 408a, 408b, 408c are positioned such that each of them is located at an apex of a triangle Δ, respectively, where the triangle Δ is defined by a first line $S_1$, a second line $S_2$, and a third line $S_3$.

In this embodiment, for notation and benefits of readers of this disclosure, it is chosen that the first leg member 408a and the second leg member 408b define a first line $S_1$ therebetween, the second leg member 408b and the third leg member 408c define a second line $S_2$ therebetween, and the third leg member 408c and the first leg member 408a define a third line $S_3$ therebetween, respectively. Other choices of the first line, the second line, and the third line can also be made; for example, one can choose that the second leg member 408b and the third leg member 408c define a first line, the third leg member 408c and the first leg member 408a define a second line, and the first leg member 408a and the second leg member 408b define a third line.

Now referring to FIGS. 4 and 5, moreover, the plate member 402 defines a passage 409 in the body portion and along a longitudinal axis A such that cross-sectionally, the center, C, of the passage 409 is located inside the triangle Δ. The passage 409 is configured, in operation, to be coincided along a planned trajectory and allow a surgical instrument, in place of a passage member 430 as illustrated in FIG. 4, to pass through the passage to reach the target of interest of the living subject.

Figure 3:
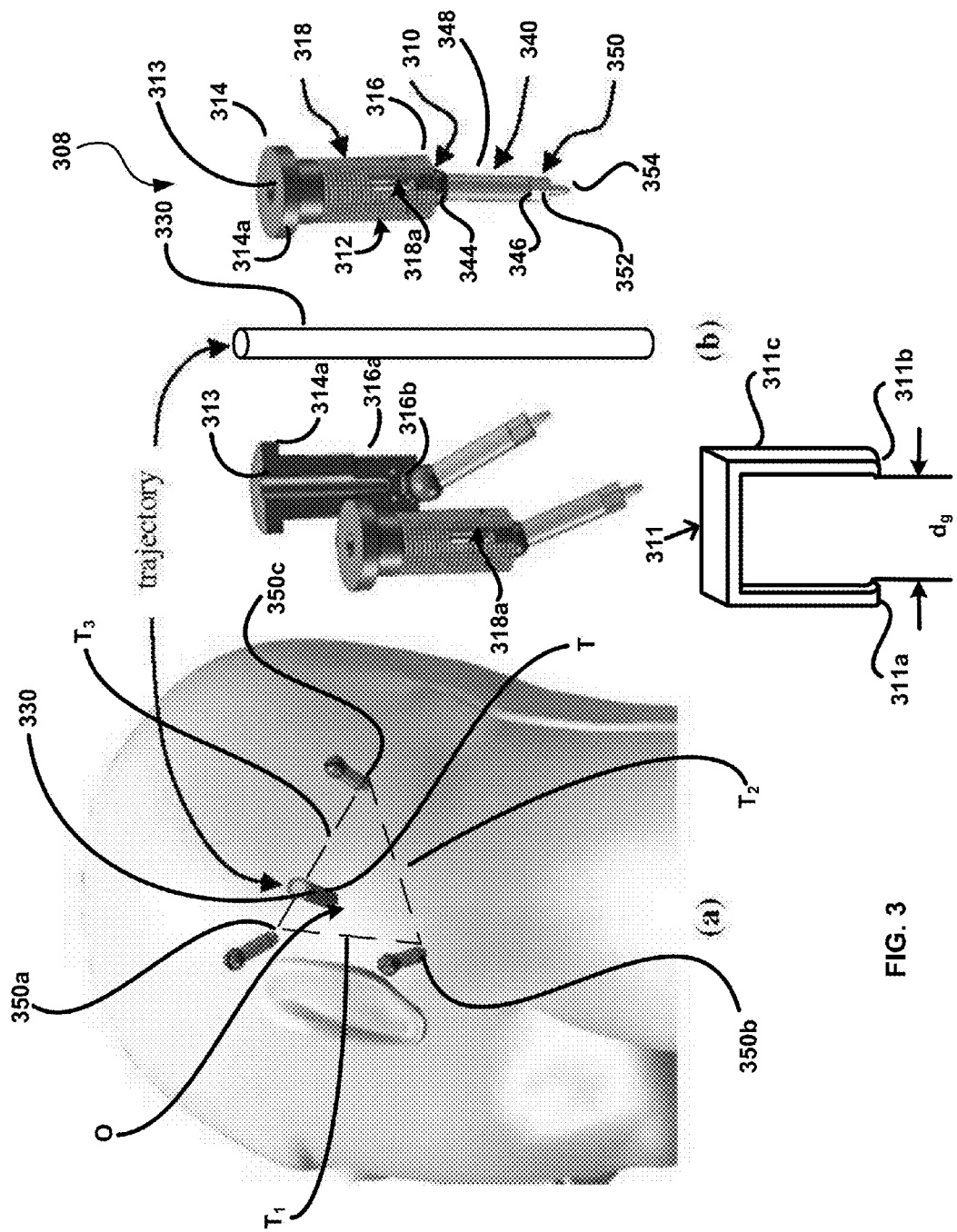
FIG. 3 shows (a) spherical fiducial markers atop extenders anchored to the skull according to one embodiment of the present invention; (b) legs or leg members attached to spherical fiducial markers according to one embodiment of the present invention. The planned trajectory is shown as a cylinder 330; (c) a perspective view of a leg member with a thumbscrew according to one embodiment of the present invention; (d) a sectional-view of (c); (e) a perspective view of a leg member (solid drawing at left; line drawing at right) with a thumbscrew according to another embodiment of the present invention; and (f) a perspective view of the leg member (solid drawing at top; line drawing at bottom) with a thumbscrew of FIG. 3(e).
Figure 3D:
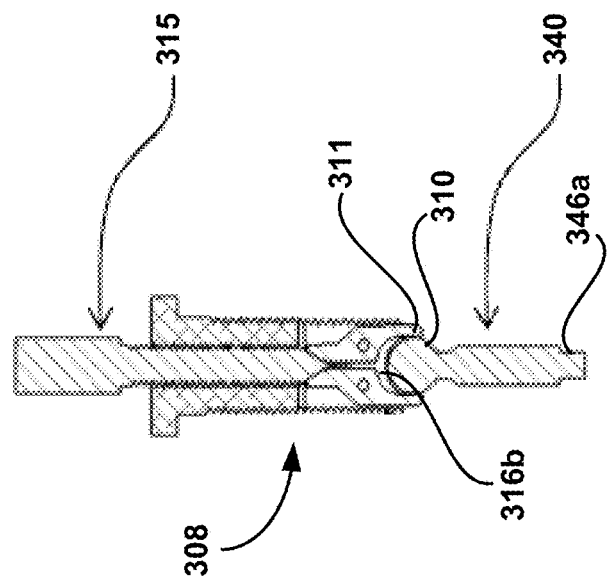
Figure 3C:
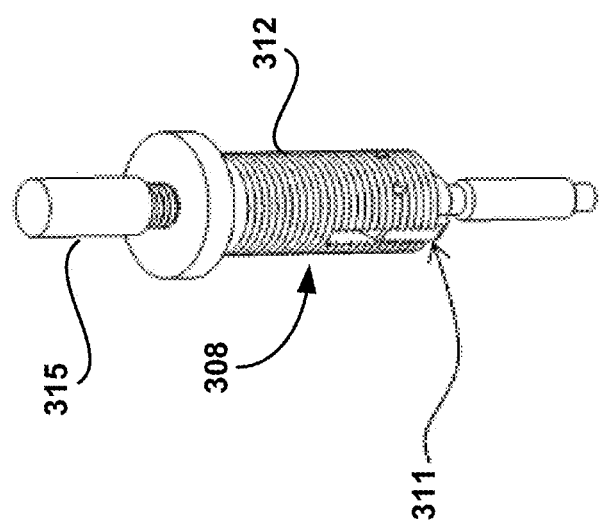
Figure 3E:
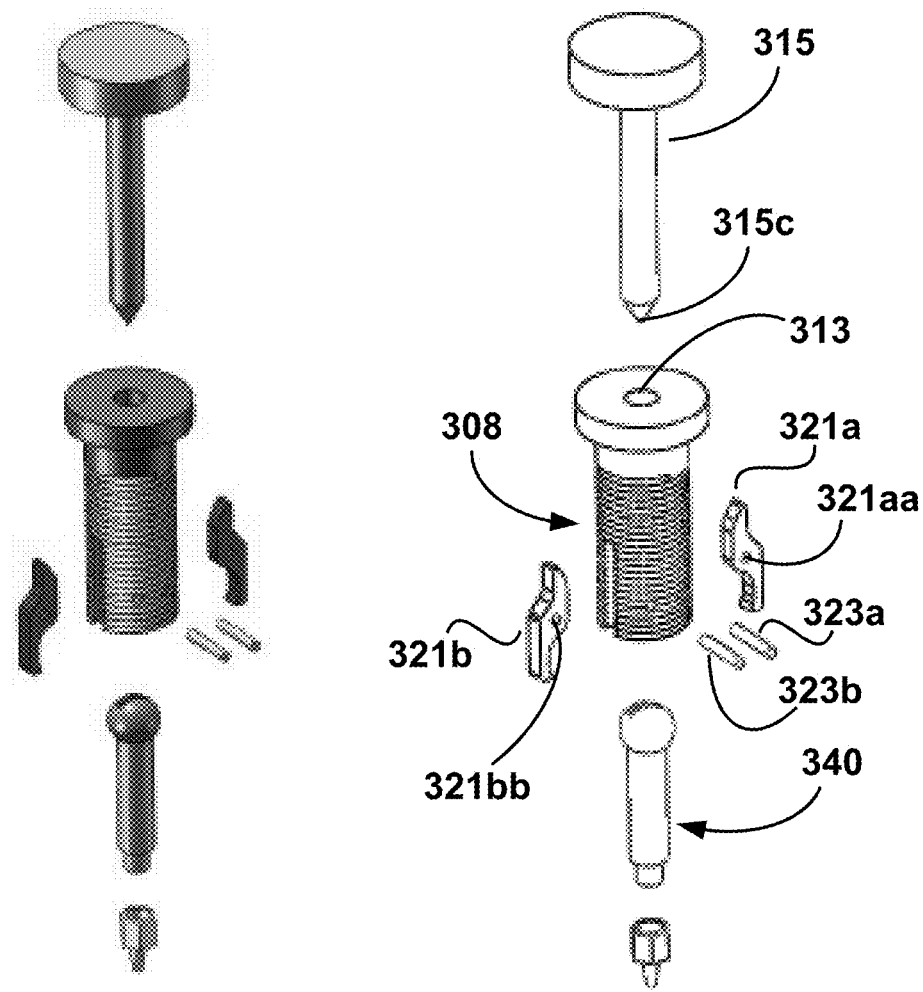

Leg members can take different forms in different embodiment. In one embodiment as shown in FIG. 3, a leg member 308 has a base member 312 that has a first end 314, and an opposite, second end 316, and a body portion 318 defined therebetween. The leg member 308 also has an extended member 340, which has a first end 344, and an opposite, second end 346, and a body portion 348 defined therebetween. The base member 312 and the extended member 340 are configured and formed such that the extended member 340 is three-dimensionally rotatably engaged at its first end 344 with the base member 312 at the second end 316 of the base member 312.

In one embodiment, the base member 312 has a cap portion 314a formed proximate to the first end 314 of the base member 312, and a bottom portion 316a formed proximate to the second end 316 of the base member 312, wherein a partially spherical recess 316b is formed in the bottom portion 316a. Moreover, the body portion 318 of the base member 312 has an opening 318a formed thereon and extending longitudinally from the second end 316 of the base member 312 towards, which may or may not reach, to the first end 314 of the base member 312. Furthermore, the base member 312 has a bore 313 formed along its longitudinal axis from the first end 314 of the base member 312 towards, which may or may not reach, to the second end 316 of the base member 312.

Figure 7:
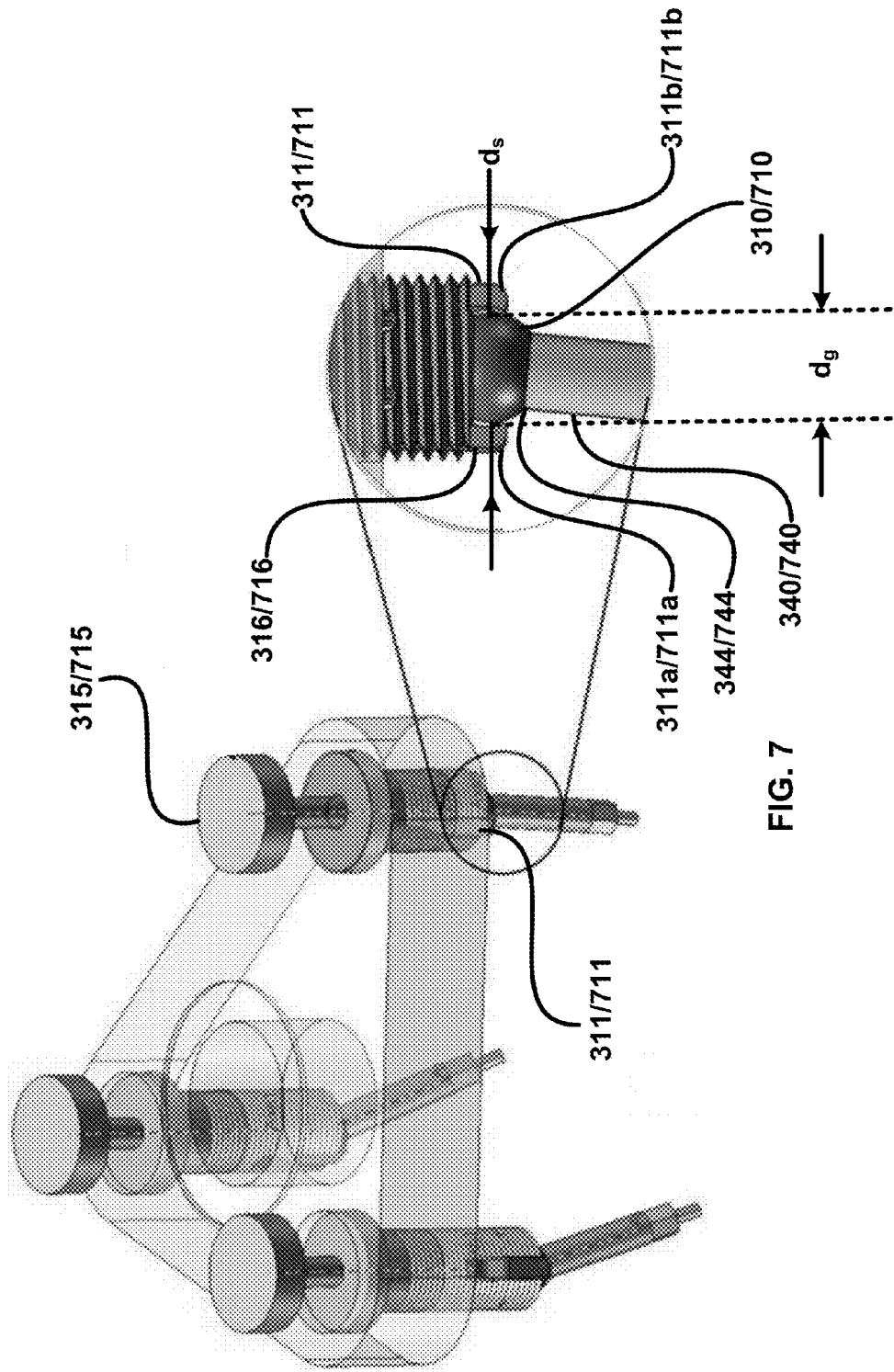
FIG. 7 shows a coupling mechanism between spherical fiducial marker and table leg according to one embodiment of the present invention. The inset shows a close up of one coupling. Twisting the thumbscrew 315/715 tightens the grippers, thereby fixing the leg to the marker.

A resilient member, which is at least partially made from a resilient material such as a metallic material, is utilized to facilitate a three-dimensionally rotatably engagement between the base member 312 and the extended member 340. Referring now to FIG. 3 and FIG. 7, a Gripper, which is identified with numeral reference number 311 in FIG. 3 and is identified with numeral reference number 311/711 in FIG. 7, respectively, is shown according to one embodiment of the present invention to facilitate a three-dimensionally rotatably engagement between the base member 312 and the extended member 340. The Gripper 311 has a first end hook portion 311a, an opposite second hook portion 311b and a base portion 311c, where the first end hook portion 311a and the second hook portion 311b project away from the base portion 311c substantially in parallel, when they are not pressed by a force, and define an opening therebetween with a distance $d_g$. The Gripper 311 is configured and formed to allow it to be received in the opening 318a of the body portion 318 with the base portion 311c being supported by the bottom portion 316a.

Furthermore, as shown in FIG. 7, when the Gripper 311/711 is received in the opening 318a of the body portion 318 of the base member 312, the first end hook portion 311a and the second hook portion 311b of the Gripper 311 are protruding beyond the second end 316/716 of the base member 312. The resilient member can take other forms as well.

Additionally, when a resilient member such as the Gripper 311/711 is received in the opening 318a of the body portion 318 of the base member 312, a tightening member can be utilized for positioning the resilient member 311. In one embodiment as shown in FIG. 3 and FIG. 7, the base member 312 has a bore 313 is formed along its longitudinal axis, and a thumbscrew 315/715, as a tightening member, is removably received in the bore 313 for tightening the Gripper 311, as a resilient member, and engaging it to the base member 312.

Still referring FIG. 3 and FIG. 7, the extended member, which is identified with numeral reference number 340 in FIG. 3 and is identified with numeral reference number 340/

740 in FIG. 7, respectively, is further described in more details herein. In this embodiment, the extended member 340/740 has an at least partially spherical top portion 310/710 formed at the first end 344/744 of the extended member 340/740, where the at least partially spherical top portion 310/710 has a diameter $d_s$. Moreover, an engagement portion 346a is formed at the second end 346 of the extended member 340 for engaging a bone anchor. The engagement portion 346a is formed with a configuration that is complimentary to the configuration of a top portion of a corresponding bone anchor for a mechanical engagement.

As can be seen particularly in FIG. 3 and FIG. 7, the at least partially spherical top portion 310, 310/710 is formed such that $d_g < d_s$. The at least partially spherical top portion 310, 310/710 of the extended member 340, 340/740 is configured to be received in a partially spherical recess 316b of the bottom portion 316a of the base member 312, such that the extended member 340 is three-dimensionally rotatable relative to the base member 312 and is also engaged at the second end 316 of the base member 312 by the first end hook portion 311a and the second hook portion 311b of the Gripper 311.

In one embodiment, as shown in FIG. 4, the base members of the first, second and third leg members 408a, 408b, 408c are substantially parallel to each other. However, the three-dimensionally rotatable engagement between each pair of the base member and corresponding extended member of a leg member allows that leg member to be attached to a bone anchor in almost any orientation. Moreover, the base members of the first, second and third leg members 408a, 408b, 408c are perpendicular to at least one of the first surface 104 and the second surface 106 of the planar plate member 102.

In one embodiment, as shown in FIGS. (3)-(6), each opening or hole, which is formed in the body portion of the plate member 402 for receiving a corresponding leg member 308/408 therein, is formed with a step that buttresses against the cap portion 314a of the base member 312 of a leg member 308 received therein. The distance from the step to the top surface of the plate member 402 is designated as Depth 1, Depth 2, and Depth 3, respectively, as illustrated particularly in FIG. 6, for the three steps formed in the holes formed in the plate member 402. Depth 1, Depth 2, and Depth 3 can be same or different, depending on a particular target of interest (i.e., a patient). Depth 1, Depth 2, and Depth 3 can be measured and calculated according to the embodiments detailed below to ensure the accuracy of the positions. As such formed, each step defines how far the cap portion of the base member of a corresponding leg member sits in the corresponding hole of the plate member 402, and the opposite end, such as the second end 316 of the base member 312 as shown in FIG. 3, of the base member of the corresponding leg member extends out of the plate member 402. Thus the depth of this step defines the effective length of the corresponding leg member to a certain degree.

The present invention, in yet another aspect, relates to a process for a making microstereotactic table usable with a surgical instrument for providing an access to a target of interest of a living subject. In one embodiment as shown in FIG. 2, the process includes the steps of providing three bone anchors such as bone anchors 350 as shown in FIG. 3, where each of the bone anchors 350 has a top portion 352 and a tip portion 354, and providing three leg members 308, where each of the leg members 308 has a base member 312, and an extended member 340 that has an at least partially spherical top portion 310 configured for rotatably and removably engagable with the base member 312 and an engagement portion 346a for engaging a bone anchor. Then at step 202, the three bone anchors are implanted into bones surrounding a target of interest T such that a first bone anchor 350a and a second bone anchor 350b define a first line $T_1$, the second bone anchor 350b and a third bone anchor 350c define a second line $T_2$, and the third bone anchor 350c and the bone anchor 350a define a third line $T_3$, where an area $\Delta$ accordingly is defined by the first line $T_1$, the second line $T_2$, and the third line $T_3$ to enclose an area O, and where the target of interest T is located inside the area O.

Optionally, the process includes a step of engaging each of the three extended members 340 with a corresponding bone anchor 350 such that each pair of an extended member 340 and a corresponding bone anchor 350 form a marker, where the center of the at least partially spherical top portion 310 of the extended member 340 of a marker represents the location of the marker. Note that the marker can be a one piece device, in which case the process so far would need only a step of implanting three markers.

At step 204, a CT scan image spanning the target of interest and all of the markers is acquired. The locations of the markers are obtained from the acquired CT scan image at step 206. In doing so, in one embodiment, the locations of the markers from the acquired CT scan image are obtained by a step of localizing the center of the at least partially spherical top portion 310 of each extended member 340.

At step 208, the location of the target of interest is obtained from the acquired CT scan image to establish a trajectory that is ending at the location of the target of interest, which is also termed as "(surgical) path planning" in the art.

Then, at 210, a microstereotactic table, or microtable, is customizedly designed by using the obtained information of the locations of the markers, the location of the target of interest and the established trajectory, where the constructed microstereotactic table comprises a plate member 402, as also shown in FIG. 5, that defines three holes, each of the three holes located at a position corresponding to a location of one of the markers, which is obtained from the acquired CT scan image. The plate member 402 further defines a passage 409 along a longitudinal axis A of the plate member 402, where the passage 409 is positioned in a path that is coincident with the trajectory.

Figure 8:
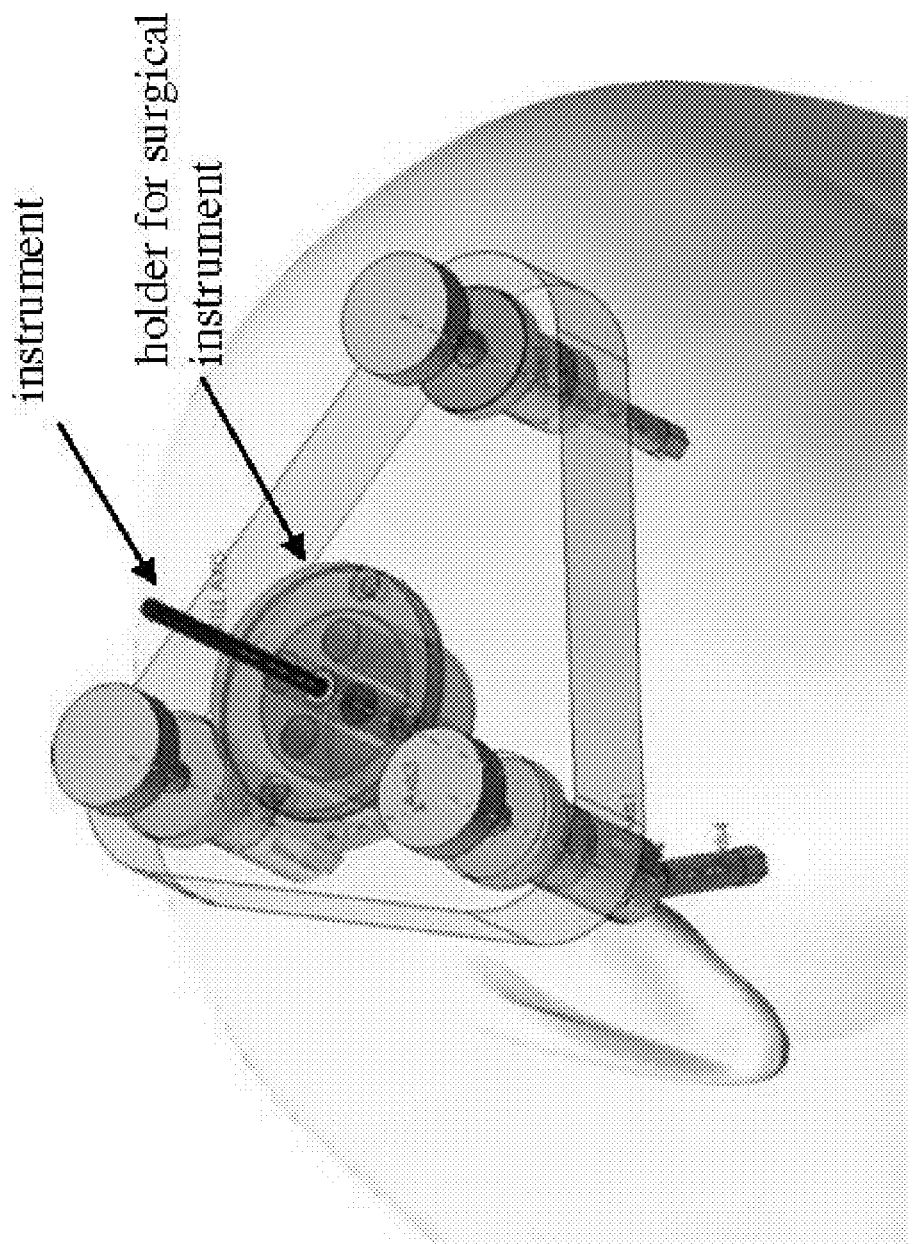
FIG. 8 shows a microstereotactic table, according to one embodiment of the present invention, attached to a patient with surgical instrument attached via a holder to the tabletop and ready for procedural intervention.
Figure 9:
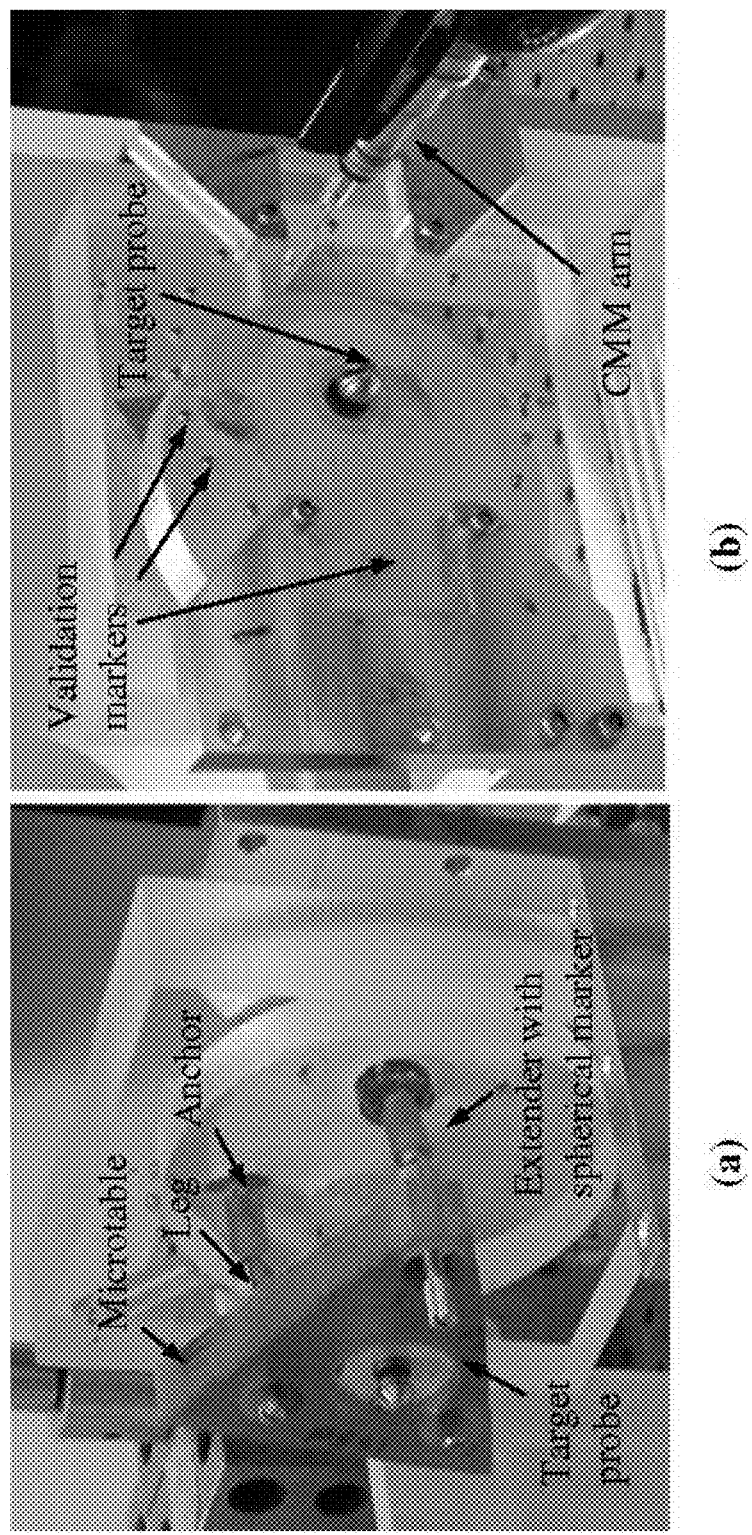
FIG. 9 shows phantom as used in coordinate measuring machine (CMM): (a) microstereotactic table mounted on the spherical markers in a phantom; (b) physical localization of spheres using the CMM.

The constructed microstereotactic table can then be sterilized at step 214, after which it can be fitted onto the implanted markers at step 216 as illustrated in FIG. 8 to allow an instrument to along the passage 409 to reach the target area. A holder may be utilized to better position or hold the instrument.

The steps set for the above can be practiced in different sequence.

These and other aspects of the present invention are further described below.

EXAMPLES AND IMPLEMENTATIONS OF THE INVENTION

Without intent to limit the scope of the invention, exemplary methods and their related results according to the embodiments of the present invention are given below. Note again that titles or subtitles may be used in the examples for convenience of a reader, which in no way should limit the scope of the invention. Moreover, certain theories may be proposed and disclosed herein; however, in no way they, whether they are right or wrong, should limit the scope of the invention.

Materials and Methods

Among other things, one aspect of the present invention is to provide a device that can allow a surgical instrument, such as a surgical drill, to reach a surgical target at the end of a specific linear trajectory. For simplicity, this surgical task is defined with two points—a target and an entry point. For building a microstereotactic frame that constrains a device to follow this path, a coordinate reference system needs to be defined in order to specify the relationship of the patient's anatomy to the frame. Thus, it is utilized a set of at least partially spherical fiducial markers, which are implanted in bone surrounding the target of interest, as a frame of reference around which all calculations can be made. One unique and central feature to the microtable according to the present invention is that these spherical fiducial markers are used to support a miniature tabletop that can be made perpendicular to the desired trajectory by specifying the length and orientation of each table leg or leg member. In one embodiment, a design is chosen in which leg members are parallel to the trajectory, which simplifies the fabrication but is not a requirement for practicing the present invention. The trajectory is located on the tabletop in reference to the legs or leg members. This embodiment is shown in its simplest implementation in FIG. 1a. To provide clearance above soft tissue, the spherical fiducial markers may be utilized in connection with extenders or extended members 140 as shown in FIG. 1b. The symmetry of the spherical fiducial markers 110 allows them to be attached to the bony anatomy with anchors 150 at relatively arbitrary locations and locations.

Referring now to FIG. 2, the steps involved for a clinical application related to the present invention are detailed as follows.

1 Implant markers—at this step, anchors are implanted into bone surrounding the surgical target of interest. For a cochlear-implant application, as an example showing how to practice the present invention, three anchors are placed in the mastoid bone surrounding the cochlea as shown in FIG. 3(*a*). Extenders are attached to the anchors with spherical fiducial markers of ¼ inch (6.35 mm) diameter at their ends. The extenders and fiducials are fashioned of CT-compatible materials. The patient is under general or local anesthesia, depending on the application.
2. Acquire CT scan—in this step, a clinically applicable CT scan is obtained spanning the surgical target and all the markers to acquire a corresponding radiographic image.
3. Localize centers of markers—at this step, the centers of the spheres are localized in the radiographic image by means of algorithms that find their intensity centroids.
4. Perform path planning—at this step, the target and entry points defining a trajectory are chosen in the CT image. This step can be performed in parallel to the localization of the markers. A fixed distance from the target is chosen as the length of the trajectory. For the embodiment shown here and this particular application, this distance is chosen as 75 mm.
5. Custom design the microtable—a customized virtual model of the microtable is created automatically by a planning software written in Matlab (The Mathworks, Natick, A, USA). The input parameters to the software are the locations of the markers as determined in Step 3 and the trajectory as specified in Step 4.

In doing so, the z-axis, or axis A in FIG. 5, is defined to be coincident with the trajectory with origin 75 mm above the surgical target and lying on the upper surface of the table (the plate member). The thickness of the table is selected based on the proposed application. In this application, a thickness ranging from 0.7 to 1 inch has been utilized. Legs extending from the tabletop to the spherical markers are chosen from a finite set of lengths (a set of three leg members used here) such that, when the foot of a leg mates with its sphere, its distal end falls within the thickness of the tabletop.

After creating the customized model, the planning software automatically generates the commands in a numerical-control programming language (G-code) to produce the required tool paths to be executed by a computer numerical-control (CNC) machine to form the tabletop.
6. Construct the microtable—at this step, under the guidance of the G-code, the CNC machine drills a hole for each leg through the tabletop perpendicular to its surface with countersinking that produces the correct depth of penetration of the legs, as calculated from the planning software, such that the tabletop is perpendicular to the trajectory and its distal surface is the required distance from the target (FIG. 4). In addition, the trajectory hole is drilled (FIG. 5).

Figure 6:
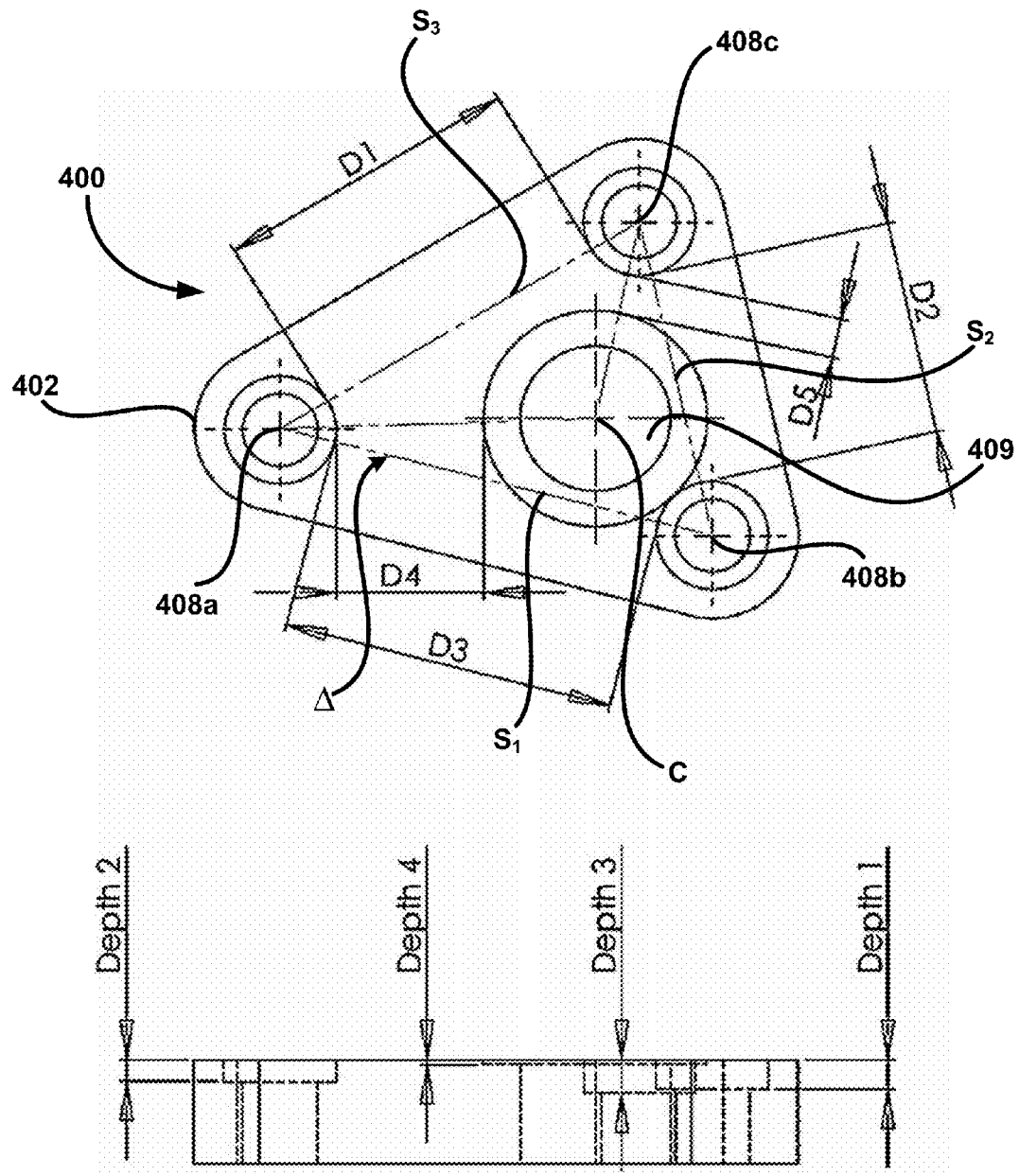
FIG. 6 shows quality assurance by measuring distances between holes according to one embodiment of the present invention.

Quality assurance is performed by inserting pins into the holes and measuring the outside-to-outside displacements of the pins relative to each other using calipers. The same is repeated at a specified height above the hole to check for parallelism. A notch on the pins at the specified height ensures repeatable measurements (FIG. 6).

Once the dimensions of the tabletop and relevant holes are determined, a two-piece cup/gripper assembly is inserted into each leg to secure each leg to its corresponding spherical fiducial marker (FIG. 7).
7. Sterilize the microtable—at this step, the assembly is flash sterilized and is ready for mounting on the patient in the procedure room.
8. Fit the microtable on the markers—at this step, the microtable is affixed to the patient and a surgical instrument such as a probe or drill is affixed to the platform in the trajectory hole (FIG. 8). A holder for the surgical instrument may be utilized.

The accuracy of the microtable can be analyzed using an approach previously used to validate the Starfix platform, as used for deep-brain stimulator placement [9,12]. The goal is to measure the accuracy with which a platform places the end of a probe at a specified target using a clinically relevant phantom. Specifically, it is measured the placement error, which is defined to be the distance by which a probe placed in the trajectory hole of the platform misses its specified target. As part of the measurement process it is necessary to determine a transformation from image space to physical space, as the target is specified in image space but is targeted in physical space. This transformation is accomplished by means of an independent registration based on 16 spherical "validation" markers not used by the microtable. Details regarding this technique of error measurement and analysis can be found in [9,12].

Phantoms were built based on the anatomy of patients, who had been enrolled in a previously reported, clinical-validation test of microstereotactic frames as used in cochlear implant surgery [13]. Each phantom (FIG. 9) was made of an acrylic block with 16 validation markers surrounding the target and three spherical fiducial markers as used to create and mount the microtable as described in the steps above. Mounting anchors for the fiducials were immobilized by embedding them in epoxy cast. The locations of the spheres can be determined either by (1) directly identifying their centers via the CT scan or (2) determining the location and orientation of the anchors and estimating their position based on the length of the extender [14]. Option 1 has the theoretical advantage of higher accuracy by direct localization of the spheres. Option 2 has the advantage that the extenders and markers do not have to be in place for the CT scan, a clinically advantageous scenario.

Two clinically applicable CT scans were made for each phantom—Option 1 with spherical fiducial marker assemblies mounted on each anchor and Option 2 with only the anchors. The 16 validation markers were localized in both CT space (using intensity-based algorithms) and physical space (using a coordinate measuring machine (CMM)) with an accuracy of 0.004 mm (Brown and Sharpe, Chameleon; Wright Industries, Nashville, Tenn.; calibration Apr. 11, 2006; certificate 4112006029735005). These localized positions were then used to produce the required transformation from image space to physical space for specifying the desired physical target. The location of this desired target is then compared to that achieved using a probe mounted on the microtable. For the present application (i.e., placing electrodes into the cochlea), the probe was 75 mm in length. Microtables were made according to the CT scans using either Option 1 or 2 as described above. The 75 mm trajectory probe was sequentially mounted in each microtable and its position measured using the CMM. The error of each microtable was calculated as the distance from the desired target position to the actual probe position. For each phantom, two microtables were analyzed—Option 1 and Option 2, respectively. The Option-1 microtable was mounted on the phantom first, as this option was expected to have better fit and less stress on the anchors, and hence less effect on the subsequent measurement for Option 2.

The Option-1 microtable was removed after the measurements were done, and the Option-2 microtable was mounted. Option 1 and Option 2 were compared using the Wilcoxon signed-rank test because (a) the data sets were related since only the fiducial marker sets differed between the two options and (b) the limited number of data points (n=5) precluded assuming a normal distribution population.

Results

Five phantoms were prepared for Option 1 and Option 2. The error values are reported in Table 1. For Option 1, the mean targeting error was 0.37±0.18 mm (n=5) with maximum error of 0.61 mm and minimum error of 0.20 mm. For Option 2, the mean targeting error was 0.60±0.21 mm (n=5) with maximum error of 0.91 mm and minimum error of 0.34 mm. Comparing results of these two options using the Wilcoxon signed-rank test showed a significant difference with Option 1 (spheres as fiducials) performing better (p=0.05). Each microtable was constructed in approximately 6 min.

TABLE 1

Error Measurements for the Microtable

| Phantom number | Option 1 | Option 2 |
|---|---|---|
| 1 | 0.20 | 0.48 |
| 2 | 0.61 | 0.64 |
| 3 | 0.26 | 0.62 |
| 4 | 0.50 | 0.91 |
| 5 | 0.27 | 0.34 |
| RMS | 0.40 | 0.63 |
| Mean ± SD | 0.37 ± 0.18 | 0.60 ± 0.21 |
| Max | 0.61 | 0.91 |
| Min | 0.20 | 0.34 |

Units are mm.
Option 1: location of spherical fiducial markers directly determined.
Options 2: location of spherical fiducial markers determined based on anchors.

Discussion

Contained herein are descriptions of, and accuracy studies of, a new microstereotactic frame based on spherical fiducial markers upon which a table is custom mounted to achieve a desired surgical trajectory. Using this device, which is termed as the "Microtable", phantom studies are performed and submillimetric accuracy is reported in conditions similar to those encountered in the human temporal bone during cochlear implant surgery. Two fiducial options are described. The first uses the spheres as the fiducials markers, and the second uses the anchors to which they attach to the patient as the fiducial markers. Using the first option, it was reported a mean accuracy of 0.37±0.18 mm (n=5). To the best of the knowledge of the inventors, this is the most accurate phantom testing yet reported for microstereotactic frames. Using the second option, it was reported an accuracy of 0.60±0.21 mm (n=5). Even in this seemly less optimal configuration, the accuracy compares favorably with those reported for other microstereotactic frames [9,11]. The first option requires that the spheres be in place during the CT scan. Hence, it requires the availability of a portable CT scanner during the procedure.

The present invention in part was motivated by the clinical goal of placing an electrode array into the cochlea via a single drill pass—a procedure known as percutaneous cochlear implantation. This radical approach to cochlear implant surgery avoids the larger surgery (mastoidectomy and posterior tympanotomy) that is the standard of care at present. This approach originally proposed in 2003 and the concept of using a customized IGS system to allow a surgeon to guide a drill along the specified trajectory was demonstrated [15]. During these original cadaver studies, it was found that the free-hand approach allowed too much room for human error. It was then moved to testing with microstereotactic frames, employing the StarFix microTargeting Platform first on cadavers [16] and subsequently performing safety testing during actual cochlear implant surgery [13]. During ongoing safety testing, it was recognized that a major impediment towards clinical application has been the need to place bone-implanted fiducial markers prior to surgical intervention such that the microstereotactic frame could be constructed via the time-consuming, and ironically-termed, "rapid"-prototyping pro-cess. It was hypothesized by the inventors an idealized work flow in which (1) bone-implanted markers could be placed at the beginning of a surgical intervention, (2) CT images could be obtained with an intraoperative CT scanner, and (3) a customized, micro-stereotactic frame could be constructed in a timely fashion (e.g., <1 h after CT scanning, which is the approximate time needed for a mastoidectomy and posterior tympanotomy).

Thus, one aspect of the present invention was to custom build—in as short a time as possible—a rigid, customized, microstereotactic frame that achieves submillimetric accuracy. Simultaneously, it was sought to do this economically. In addition to the unsurpassed accuracy, it is the combination of these two characteristics—speed and cost—that differentiate the microtable according to the present invention from others that are clinically available. As noted above, the two microstereotactic frames to which the microtable is compared are the StarFix microTargeting Platform and the NexFrame. The StarFix micro Targeting Platform has an impressive accuracy of 0.45±0.15 mm for even deeper targets (120 mm) [9], but it takes hours for fabrication via rapid prototyping technology. The current workflow for a Starfix includes electronic transmission of data sets to a centralized manufacturing facility. As a result, in clinical practice the Starfix platform has a minimum 48-h turn-around time. The NexFrame, though it does not impose this time delay, requires intraoperative adjustments with the help of an expensive IGS system.

Unique to the microtable described herein is its capability for rapid targeting, resulting from the simple expedient of drilling a set of parallel holes through a single planar tabletop, which then mounts to a set of standardized table legs. Fabrication of the tabletop is the only varying component in the production of a microtable. Tabletop customization is achieved by drilling holes of specified depth and radius at the precise location at which the legs intersect the tabletop. To do this, as described in the "Materials and methods" section, it was utilized a CNC milling machine. However, the versatility of a milling machine is in fact not required for this relatively simple application. A drill press combined with an x-y positioning table could achieve the same results. By using a CNC machine, however, it was able to automate the fabrication process reducing the possibility of human error. In addition, the CNC machine allows one to fabricate the microtable in approximately 6 min, justifying the moderate expense (approximately $15,000). Obviated is the need for either an IGS system (approximately $100,000), as required by the NexFrame, or an accurate rapid prototyping machine (approximately $50,000), as required by the Starfix.

Clinical data gathered so far, albeit limited, shows a turnaround time—from CT scanning after fiducial markers are placed until complete assembly of a microtable—of under 45 min. This total time includes automated localization of the fiducial markers in the CT scan [14], automated planning of the surgical trajectory [17], generation of a virtual model of the microtable, translation of the virtual model to the CNC's input language, fabrication of the tabletop, quality assurance, attachment to the tabletop of legs with grippers used to fix the tabletop to the spherical fiducial markers, and labeling of the entire assembly to provide orientation. Anticipating 10-15 min of sterilization time, one can conservatively estimate that a microtable can be made in less than 1 h.

Figure 10:
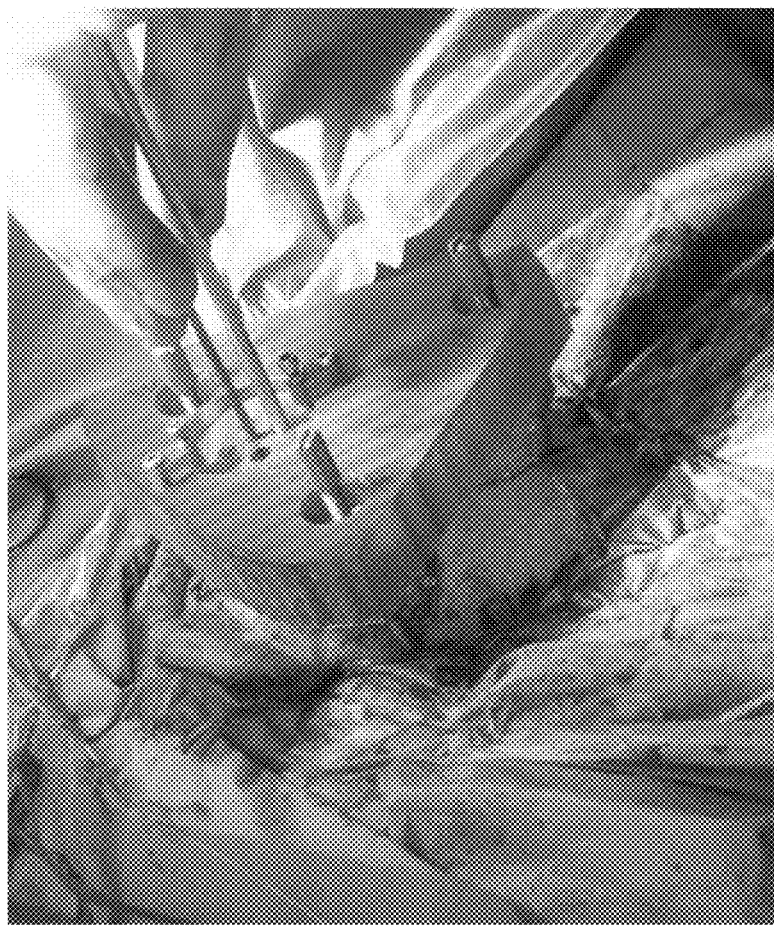
FIG. 10 shows a microstereotactic table, according to one embodiment of the present invention, mounted on the patient's head for validation. The microstereotactic table was fabricated intraoperatively for cochlear implantation for the patient.

Eleven clinical validation procedures using the microtable have been performed (a snap shot of one such clinical validation procedure is shown in FIG. 10). All have been clinically successful [18]. It is evident that the upper limit of accuracy that can be clinically achieved using the microtable according to the present invention, is submillimetric. While clinically intended for percutaneous cochlear implant surgery, other potential applications would include placement of deep brain stimulators and targeting tissue for biopsy purposes.

The foregoing description of the exemplary embodiments of the invention has been presented only for the purposes of illustration and description and is not intended to be exhaustive or to limit the invention to the precise forms disclosed. Many modifications and variations are possible in light of the above teaching.

For examples, although exemplary various embodiments are set forth above and in the accompanying drawings with a configuration where there are three leg members utilized in connection with a microstereotactic table. The present invention, in fact, can be practiced in connection with a microstereotactic table that has three or more leg members, or a plurality of leg members.

Figure 4B:
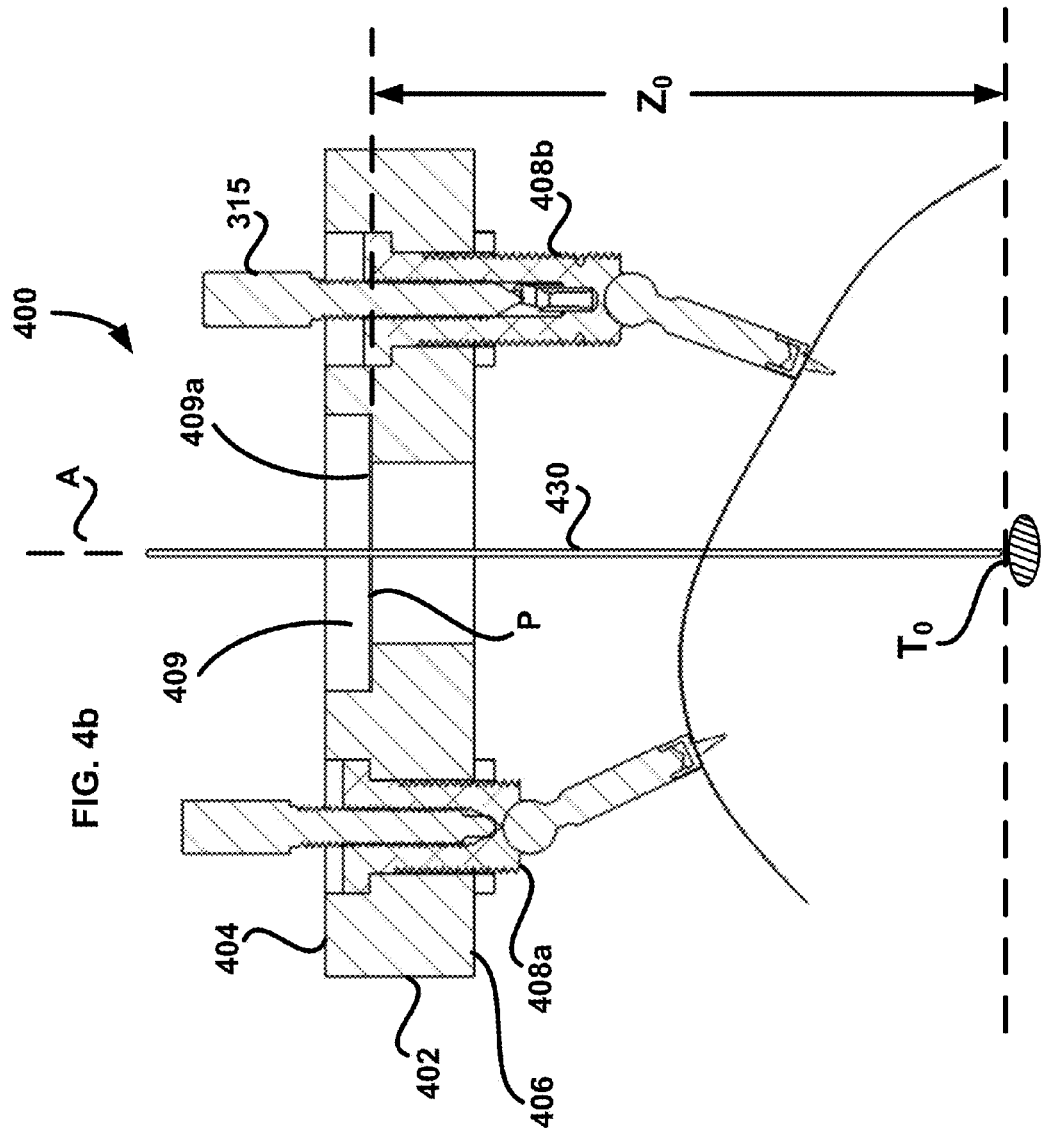

Thus, the present invention, in another aspect, relates to a microstereotactic table that has a plate member having a first surface, an opposite, second surface, a body portion defined therebetween. Moreover, the microstereotactic table has a plurality of leg members, each of them removably engaged with the plate member, respectively. Furthermore, as shown in FIG. 4(b), a passage 409 is formed between the first surface 404 and the opposite, second surface 406 of the body portion of the plate member 402 and along a longitudinal axis A. Additionally, a step 409a is formed within the passage 409 such that the portion of the passage 409 between the first surface 404 and the step 409a has a diameter that is larger than that of the portion of the passage 409 between the second surface 406 and the step 409a. In this configuration, the microstereotactic table 400 is positioned in operation such that the second surface faces the target of interest $T_0$. For the embodiment as shown in FIG. 4(b), the step 409a is formed with a planar surface such that the distance, $Z_0$, from the step 409a to the target of interest $T_0$ is a predetermined length. The planar surface of the step 409a functions as a reference plane P that allows a surgical instrument to pass through to not only reach the target of the interest but to stop at the target, which for example can be achieved such that the advancement of the surgical instrument towards to the target of the interest will be stopped when, for example, a certain part of the surgical instrument reaches the step 409a and becomes buttressed by the step 409a. In one embodiment as set forth above, this predetermined distance, $Z_0$, between the reference plane P and the target of interest $T_0$ is chosen as 75 mm. Alternatively, one of the first surface and the opposite, second surface along the longitudinal axis A, or in fact any plane perpendicular to the longitudinal axis A can be chosen as a reference plane to which the base members of the leg members are perpendicular, respectively. As such, the plane chosen as the reference place has a distance from it to the target of interest, which is a predetermined length.

In one embodiment, each of the plurality of leg members has a base member, and an extended member, wherein the base member and the extended member are configured such that the extended member is three-dimensionally rotatably engaged with the base member.

The base member has a cap portion formed proximate to a first end of the base member, and a bottom portion formed proximate to an opposite, second end of the base member, wherein a partially spherical recess is formed in the bottom portion. The base member further has a body portion that has an opening formed thereon and extending longitudinally from the second end of the base member towards to the first end of the base member, and a resilient member configured to be received in the opening of the body portion and defining an opening. The base member, moreover, has a bore formed along its longitudinal axis.

The extended member further has an at least partially spherical top portion formed at the first end of the extended member, and an engagement portion formed at the second end of the extended member for engaging a bone anchor. The at least partially spherical top portion of the extended member is configured to be received in the partially spherical recess of the bottom portion of the base member, such that the extended member is three-dimensionally rotatable relative to the base member and is also engaged at the second end of the base member by the resilient member.

The resilient member, in one embodiment, is a gripper having a first end hook portion, an opposite second hook portion and a base portion, wherein the first end hook portion and the second hook portion project away from the base portion in parallel and define an opening therebetween. The gripper can take various forms. For example, in one embodiment as shown in FIG. 3(b), a resilient member in the form of gripper 311 is illustrated.

In another embodiment as shown in FIGS. 3(c)-3(f), a resilient member in the form of gripper 321 is also illustrated. In this embodiment, gripper 321 has a first member 321a that has a slopped top portion 333a, a hook portion projecting away from the slopped top portion 333a, and a pin-hole 321aa formed therebetween. The gripper 321 also has a second member 321b that has a slopped top portion 333b, a hook portion projecting away from the slopped top portion 333b, and a pin-hole 321bb formed therebetween. The gripper 321 is configured and formed to allow it to be received in the opening 318a of the body portion of the base member 312 of the leg member 308 such that the first member 321a and the second member 321b are symmetrical about the longitudinal axis. A first pin 323a and a second pin 323b are utilized to penetrate through the pin-hole 321aa and the pin-hole 321bb, respectively, to pin the gripper 321 to the leg member 308.

Figure 3F:
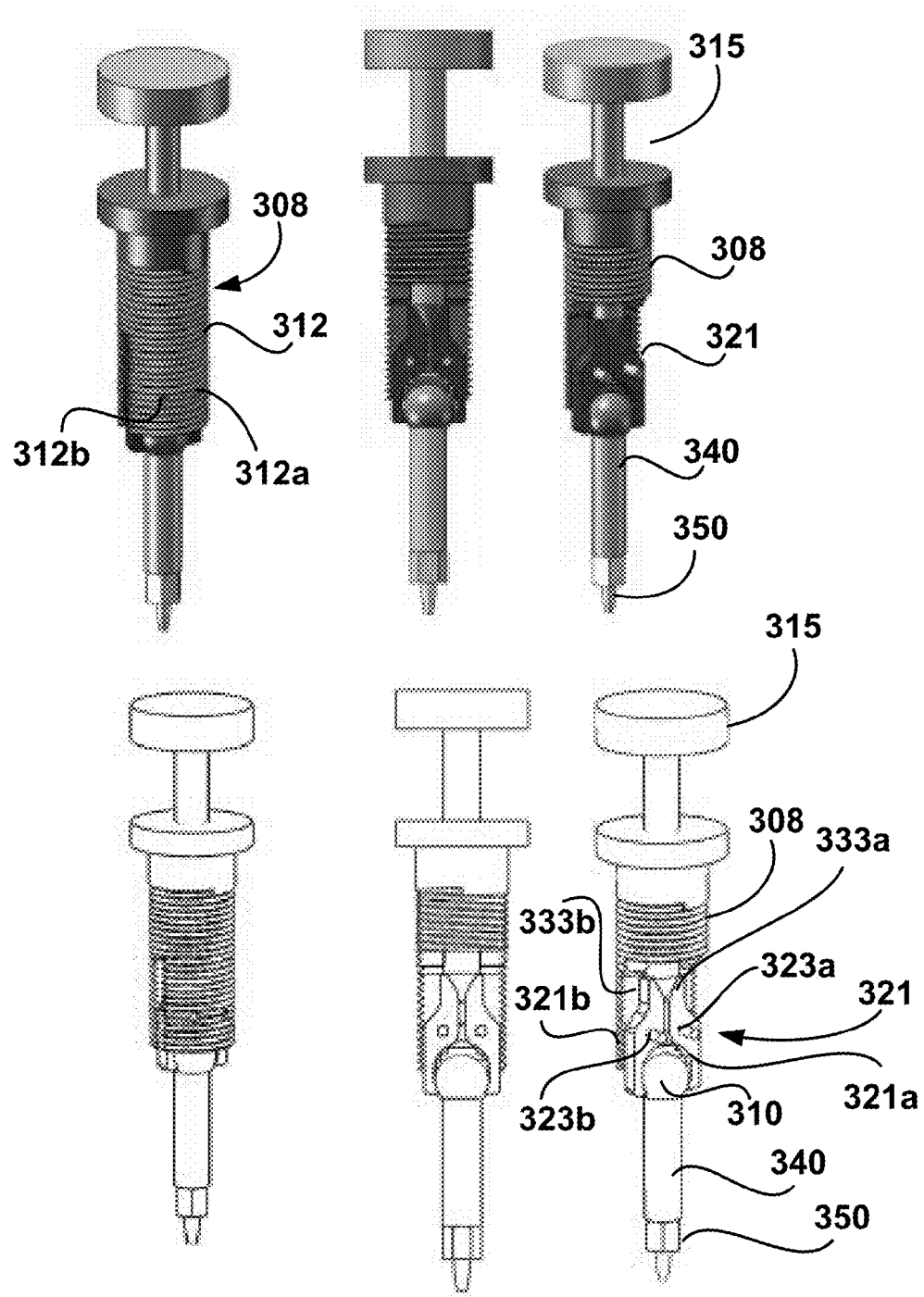

A tightening member is removably received in the bore for positioning/tightening the resilient member. In one embodiment, the tightening member is a thumbscrew 315. As shown in FIG. 3(f), for this embodiment, when the thumbscrew 315 is screwed such that the tip portion of the thumbscrew 315 penetrates into therebetween the slopped top portion 333a of the first member 321a and the slopped top portion 333b of the second member 321b, the tip portion of the thumbscrew 315 forces the slopped top portion 333a and the slopped top portion 333b apart, i.e., each slightly making a rotation around a corresponding pin in opposite direction, which results in the bottom hook portions moving towards each other to grip the at least partially spherical top portion 310 of the extended member 340.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

References

1. Maurer C R Jr, Fitzpatrick J M, Wang M Y et al (1997) Registration of head volume images using implantable fiducial markers. IEEE Trans Med Imaging 16:447-462. doi:10.1109/42.611354.
2. Woerdeman P A, Willems P W A, Noordmans H J et al (2007) Application accuracy in frameless image-guided neurosurgery: a comparison study of three patient-to-image registration methods. J Neurosurg 106(6):1012-1016. Doi:10.3171/jns.2007.106.6.1012
3. Brown R A (1986) System using computed tomography as for selective body treatment. U.S. Pat. No. 4,608,977, US Patent and Trademark Office (filed 1982, granted 1986).
4. Maciunas R J, Galloway R L Jr, Latimer J W (1994) The application accuracy of stereotactic frames. Neurosurgery 35:682-694. doi:10. 1097/00006123-199410000-00015.
5. Yu C, Apuzzo M L, Zee C S, Petrovich Z (2001) A phantom study of the geometric accuracy of computed tomographic and magnetic resonance imaging stereotactic localization with the Leksell stereotactic system. Neurosurgery 48:1092-1099. doi:10.1097/00006123-200105000-00025.
6. Bjartmarz H, Rehncrona S (2007) Comparison of accuracy and precision between frame-based and frameless stereotactic navigation for deep brain stimulation electrode implantation. Stereotact Funct Neurosurg 85:235-242. doi: 10.1159/000103262.
7. Franklin R J, Franck J I, Haer F C (2001) Customized surgical fixture. U.S. Pat. No. 6,327,491, US Patent and Trademark Office (filed 1998, granted 2001).
8. Franck J, Konrad P, Franklin R et al (2002) STarFix: a novel approach to frameless stereotactic neurosurgery utilizing a miniaturized customized pretargeted cranial platform fixture—technical description, unique features, and case reports. Movement Disorders Society. In: Seventh international congress of parkinsons disease and movement disorder, Miami.
9. Balachandran R, Mitchell J, Dawant B M, Fitzpatrick J M (2009) Accuracy evaluation of MicroTargeting™ platforms for deep-brain stimulation using virtual targets. IEEE Trans Biomed Eng 56(1):37-44.
10. Franck J I, Haer F C, Franklin R J et al (2001) Instrument guidance for stereotactic surgery. U.S. Pat. No. 6,298,262, US Patent and Trademark Office (filed May 2001, granted October 2001).
11. Henderson J M, Holloway K L, Gaede S E, Rosenow J M (2004) The application accuracy of a skull-mounted trajectory guide system for image-guided functional neurosurgery. Comput Aided Surg 9:155-160. doi:10.1080/10929080500050249.
12. Balachandran R, Mitchell J, Dawant B, Fitzpatrick J M (2007) Evaluation of targeting frames for deep-brain stimulation using virtual targets. In: IEEE international symposium on biomedical imaging: from Nano to Macro, 2007, pp 1184-1187.
13. Labadie R F, Noble J H, Dawant B M et al (2008) Clinical validation of percutaneous cochlear implant surgery: Initial report. Laryngoscope 118(6):1031-1039.
14. Liu X, Cevikalp H, Fitzpatrick J M (2003) Marker orientation in fiducial registration. In: Proceedings SPIE Medical Imaging 2003, San Diego, Calif., vol 5032. pp 1176-1185.
15. Labadie R F, Choudhury P, Cetinkaya E et al (2005) Minimally-invasive, image-guided, facial-recess approach to the middle ear: Demonstration of the concept of percutaneous cochlear access in vitro. Otol Neurotol 26:557-562. doi:10.1097/01.mao. 0000178117.61537.5b.
16. Warren F M, Balachandran R, Fitzpatrick J M, Labadie R F (2007) Percutaneous cochlear access using bone-mounted, customized drill guides: demonstration of concept in vitro. Otol Neurotol 28(3):325-329. Doi:10.1097/01.mao.0000253287.86737.2e.
17. Noble J H, Warren F M, Labadie R F et al (2007) Determination of drill paths for percutaneous cochlear access accounting for target positioning error. In: Proceedings of Medical Imaging 2007, San Diego.
18. Labadie R F, Balachandran R, Mitchell J et al (2009) Clinical validation study of percutaneous cochlear access using patient-customized, microstereotactic frames. Accepted for presentation at the 2009 AOS/COSM Spring Meeting Scientific Sessions, Phoenix, Ariz., May 2009.

What is claimed is:

1. A microstereotactic table usable with a surgical instrument for providing an access to a target of interest of a living subject, comprising:
    (a) a planar plate member having a first surface, an opposite, second surface, a body portion defined therebetween;
    (b) a first leg member removably engaged with the planar plate member;
    (c) a second leg member removably engaged with the planar plate member; and
    (d) a third leg member removably engaged with the planar plate member, wherein the first, second and third leg members are positioned such that each of them is located at an apex of a triangle Δ, respectively, wherein the first leg member and the second leg member define a first line $S_1$, the second leg member and the third leg member define a second line $S_2$, and the third leg member and the first leg member define a third line $S_3$, and wherein the triangle Δ is defined by the first line $S_1$, the second line $S_2$, and the third line $S_3$,
        wherein the planar plate member defines a passage between the first surface and the second surface of the body portion and along a longitudinal axis A, wherein cross-sectionally the center of the passage is located inside the triangle Δ, and wherein the passage is configured, in operation, to be coincided along a planned trajectory and allow a surgical instrument to pass through the passage to reach the target of interest of the living subject, and wherein each of the first, second and third leg members comprises:

a base member having a first end, and an opposite, second end, a body portion defined between the first and second ends, a cap portion formed proximate to the first end, a bottom portion formed proximate to the second end, a bore formed through the body portion along its longitudinal axis, a gripper, and a thumbscrew that is removably received in the bore for tightening the gripper, the body portion having an opening formed therein and extending longitudinally from the second end towards to the first end, the bottom portion having a partially spherical recess formed therein, and the gripper being received in the opening of the body portion in the bottom portion; and an extended member having a first end, and an opposite, second end, a body portion defined therebetween, and an at least partially spherical top portion formed at the first end, wherein the base member and the extended member are configured such that the extended member is three-dimensionally rotatably engaged at its first end with the base member at the second end of the base member; and wherein the gripper has a first member and a second member, each member having a sloped top portion, a hook portion projecting away from the sloped top portion, and a pin-hole formed therebetween, configured to allow it to be received in the opening of the body portion of the base member of the leg member such that the first member and the second member are symmetrical about the longitudinal axis, and wherein as assembled, a first pin and a second pin are utilized to penetrate through the pin-holes of the first and second members, respectively, to pin the gripper to the leg member, and the thumbscrew is removably received in the bore of the base member such that the tip portion of the thumbscrew penetrates into therebetween the sloped top portions of the first and second members and forces the sloped top portions of the first and second members apart, thereby, resulting in the bottom hook portions of the first and second members moving towards each other to grip the at least partially spherical top portion of the extended member.

2. The microstereotactic table of claim 1, wherein the extended member further comprises:

an engagement portion formed at the second end of the extended member for engaging a bone anchor.

3. The microstereotactic table of claim 2, wherein the at least partially spherical top portion of the extended member is configured to be received in the partially spherical recess of the bottom portion of the base member, such that the extended member is three-dimensionally rotatable relative to the base member and is also engaged at the second end of the base member by the gripper.

4. The microstereotactic table of claim 3, wherein the engagement portion formed at the second end of the extended member is formed with a configuration that is complimentary to the configuration of a top portion of a corresponding bone anchor for a mechanical engagement.

5. The microstereotactic table of claim 1, wherein the base members of the first, second and third leg members are parallel to each other.

6. The microstereotactic table of claim 5, wherein the base members of the first, second and third leg members are perpendicular to at least one of the first surface and the second surface of the planar plate member.

7. A leg member for supporting a microstereotactic table, comprising:

(a) a base member having a first end, and an opposite, second end, a body portion defined between the first and second ends, a cap portion formed proximate to the first end, a bottom portion formed proximate to the second end, a bore formed through the body portion along its longitudinal axis, a gripper, and a tightening member that is removably received in the bore for positioning the gripper, the body portion having an opening formed therein and extending longitudinally from the second end towards to the first end, the bottom portion having a partially spherical recess formed therein, and the gripper being received in the opening of the body portion in the bottom portion; and (b) an extended member having a first end, and an opposite, second end, a body portion defined therebetween, and an at least partially spherical top portion formed at the first end, wherein the base member and the extended member are configured such that the extended member is three-dimensionally rotatably engaged at its first end with the base member at the second end of the base member;

wherein the gripper has a first member and a second member, each member having a sloped top portion, a hook portion projecting away from the sloped top portion, and a pin-hole formed therebetween, configured to allow it to be received in the opening of the body portion of the base member of the leg member such that the first member and the second member are symmetrical about the longitudinal axis, and wherein as assembled, a first pin and a second pin are utilized to penetrate through the pin-holes of the first and second members, respectively, to pin the gripper to the leg member, and the tightening member is removably received in the bore of the base member such that the tip portion of the tightening member penetrates into therebetween the sloped top portions of the first and second members and forces the sloped top portions of the first and second members apart, thereby, resulting in the bottom hook portions of the first and second members moving towards each other to grip the at least partially spherical top portion of the extended member.

8. The leg member of claim 7, wherein the extended member further comprises:

an engagement portion formed at the second end of the extended member for engaging a bone anchor.

9. The leg member of claim 8, wherein the at least partially spherical top portion of the extended member is configured to be received in the partially spherical recess of the bottom portion of the base member, such that the extended member is three-dimensionally rotatable relative to the base member and is also engaged at the second end of the base member by the gripper.

10. The leg member of claim 7, wherein the tightening member is a thumbscrew.

11. The leg member of claim 9, wherein the engagement portion formed at the second end of the extended member is formed with a configuration that is complimentary to the configuration of a top portion of a corresponding bone anchor for a mechanical engagement.

* * * * *